US009284370B1

(12) United States Patent
Medich et al.

(10) Patent No.: US 9,284,370 B1
(45) Date of Patent: *Mar. 15, 2016

(54) METHODS FOR TREATING JUVENILE IDIOPATHIC ARTHRITIS

(71) Applicant: AbbVie Biotechnology Ltd., Hamilton (BM)

(72) Inventors: John R. Medich, Highland Park, IL (US); Susan K. Paulson, Downers Grove, IL (US); Peter A. Noertersheuser, Gro-Karlbach (DE)

(73) Assignee: AbbVie Biotechnology Ltd., Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 14/679,476

(22) Filed: Apr. 6, 2015

Related U.S. Application Data

(63) Continuation of application No. 12/157,599, filed on Jun. 10, 2008, now Pat. No. 8,999,337.

(60) Provisional application No. 61/066,943, filed on Feb. 25, 2008, provisional application No. 61/002,125, filed on Nov. 5, 2007, provisional application No. 60/934,310, filed on Jun. 11, 2007.

(51) Int. Cl.
*A61K 39/00* (2006.01)
*A61K 39/395* (2006.01)
*C07K 16/24* (2006.01)
*A61K 31/155* (2006.01)

(52) U.S. Cl.
CPC ............. *C07K 16/241* (2013.01); *A61K 31/155* (2013.01); *A61K 39/3955* (2013.01)

(58) Field of Classification Search
None
See application file for complete search history.

(56) References Cited

U.S. PATENT DOCUMENTS

| | | |
|---|---|---|
| 5,231,024 A | 7/1993 | Moeller et al. |
| 5,336,181 A | 8/1994 | Nakao et al. |
| 5,654,407 A | 8/1997 | Boyle et al. |
| 5,656,272 A | 8/1997 | Le et al. |
| 5,672,347 A | 9/1997 | Aggarwal et al. |
| 5,698,195 A | 12/1997 | Le et al. |
| 5,705,389 A | 1/1998 | Braham et al. |
| 5,795,967 A | 8/1998 | Aggarwal et al. |
| 5,859,205 A | 1/1999 | Adair et al. |
| 5,877,293 A | 3/1999 | Adair et al. |
| 5,888,511 A | 3/1999 | Skurkovich et al. |
| 5,929,212 A | 7/1999 | Jolliffe et al. |
| 5,945,098 A | 8/1999 | Sarno et al. |
| 5,958,953 A | 9/1999 | Marfat |
| 5,994,510 A | 11/1999 | Adair et al. |
| 6,015,557 A | 1/2000 | Tobinick et al. |
| 6,024,938 A | 2/2000 | Corbo et al. |
| 6,090,382 A | 7/2000 | Salfeld et al. |
| 6,171,586 B1 | 1/2001 | Lam et al. |
| 6,177,077 B1 | 1/2001 | Tobinick |
| 6,214,870 B1 | 4/2001 | McClure et al. |
| 6,235,281 B1 | 5/2001 | Stenzel et al. |
| 6,258,562 B1 | 7/2001 | Salfeld et al. |
| 6,270,766 B1 | 8/2001 | Feldman et al. |
| 6,306,820 B1 | 10/2001 | Bendele et al. |
| 6,379,666 B1 | 4/2002 | Tobinick |
| 6,419,944 B2 | 7/2002 | Tobinick |
| 6,423,321 B2 | 7/2002 | Tobinick |
| 6,448,380 B2 | 9/2002 | Rathjen et al. |
| 6,451,983 B2 | 9/2002 | Rathjen et al. |
| 6,498,237 B2 | 12/2002 | Rathjen et al. |
| 6,509,015 B1 | 1/2003 | Salfeld et al. |
| 6,537,549 B2 | 3/2003 | Tobinick |
| 6,562,006 B1 | 5/2003 | Hjertman et al. |
| 6,593,458 B1 | 7/2003 | Rathjen et al. |
| 7,070,775 B2 | 7/2006 | Le et al. |
| 7,153,507 B2 | 12/2006 | van de Winkel et al. |
| 7,192,584 B2 | 3/2007 | Le et al. |
| 7,223,394 B2 | 5/2007 | Salfeld et al. |
| 7,223,397 B1 | 5/2007 | Rosenblum et al. |
| 7,250,165 B2 | 7/2007 | Heavner et al. |
| 7,276,239 B2 | 10/2007 | Le et al. |
| 7,521,206 B2 | 4/2009 | Heavner et al. |
| 7,541,031 B2 | 6/2009 | Salfeld et al. |
| 7,582,742 B2 | 9/2009 | Masat et al. |
| 7,588,761 B2 | 9/2009 | Salfeld et al. |
| 7,691,378 B2 | 4/2010 | Heavner et al. |
| 7,728,114 B2 | 6/2010 | Mach et al. |

(Continued)

FOREIGN PATENT DOCUMENTS

| | | |
|---|---|---|
| EP | 0101681 | 3/1984 |
| EP | 0186833 | 7/1986 |

(Continued)

OTHER PUBLICATIONS

"Enbrel: EPAR—Scientific Discussion," (Oct. 18, 2006), 1-42, Retrieved from the Internet: URL:http://www.ema.europa. eujdocsjen GB/document library/EPAR- Scientific Discussion/human/000262/WC500027358.pdf—[retrieved on Oct. 28, 2011].
[online] Statement on a Nonproprietary Name Adopted by the USAN Council: Adalimumab, [retrieved on May 19, 2011] Retrieved from: www.amaassn.org/resources/doc/usan/adalimumab.doc, p. 1.
Anthony et al., "Pain in children with arthritis: a review of the current literature," Arthritis Rheum., 49(2):272-9 (2003).
Asadullah et al., "A high prevalence of cytomegalovirus antigenaemia in patients with moderate to severe chronic plaque psoriasis: an association with systemic tumor necrosis factor α overexpression," Br. J. Dermatol, 141(1):94-102 (1999).
Baeten et al., "Immunomodulatory effects of anti-tumor necrosis factor alpha therapy on synovium in spondylarthropathy: histologic findings in eight patients from an open-label pilot study," Arthritis & Rheumatism, 44(1):186-195 (2001).

(Continued)

*Primary Examiner* — Shulamith H Shafer
(74) *Attorney, Agent, or Firm* — Foley Hoag LLP

(57) ABSTRACT

The invention provides methods and compositions for the treatment of juvenile idiopathic arthritis (JIA) where a TNFα inhibitor, such as a human TNFα antibody, or antigen-binding portion thereof, is used to treat JIA. In particular, the invention is directed to methods and compositions relating to a fixed dosing regimen for treating JIA with a TNFα inhibitor.

38 Claims, 5 Drawing Sheets

(56) References Cited

U.S. PATENT DOCUMENTS

| | | |
|---|---|---|
| 7,863,426 B2 | 1/2011 | Wan et al. |
| 7,919,264 B2 | 4/2011 | Maksymowych et al. |
| 8,034,906 B2 | 10/2011 | Borhani et al. |
| 8,092,998 B2 | 1/2012 | Stuhlmuller et al. |
| 8,093,045 B2 | 1/2012 | Pla et al. |
| 8,187,836 B2 | 5/2012 | Hsieh |
| 8,197,813 B2 | 6/2012 | Salfeld et al. |
| 8,206,714 B2 | 6/2012 | Salfeld et al. |
| 8,216,583 B2 | 7/2012 | Kruase et al. |
| 8,231,876 B2 | 7/2012 | Wan et al. |
| 8,372,400 B2 | 2/2013 | Salfeld et al. |
| 8,420,081 B2 | 4/2013 | Fraunhofer et al. |
| 8,636,704 B2 | 1/2014 | Shang et al. |
| 8,679,061 B2 | 3/2014 | Julian et al. |
| 8,715,664 B2 | 5/2014 | Hoffman et al. |
| 8,753,839 B2 | 6/2014 | Fraunhofer et al. |
| 8,846,046 B2 | 9/2014 | Kaymakcalan et al. |
| 8,889,135 B2 | 11/2014 | Fischkoff et al. |
| 8,889,136 B2 | 11/2014 | Hoffman et al. |
| 2001/0021380 A1 | 9/2001 | Pluenneke |
| 2003/0012786 A1 | 1/2003 | Teoh et al. |
| 2003/0161828 A1 | 8/2003 | Abdelghany et al. |
| 2003/0206898 A1 | 11/2003 | Fischkoff et al. |
| 2003/0219438 A1 | 11/2003 | Salfeld et al. |
| 2004/0009172 A1 | 1/2004 | Fischkoff et al. |
| 2004/0033228 A1 | 2/2004 | Krause et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136988 A1 | 7/2004 | Skurkovich et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0219142 A1 | 11/2004 | Banerjee et al. |
| 2005/0249735 A1 | 11/2005 | Le et al. |
| 2006/0018907 A1 | 1/2006 | Le et al. |
| 2006/0083741 A1 | 4/2006 | Hoffman et al. |
| 2006/0246073 A1 | 11/2006 | Knight et al. |
| 2007/0041905 A1 | 2/2007 | Hoffman et al. |
| 2007/0081996 A1 | 4/2007 | Hoffman et al. |
| 2007/0196373 A1 | 8/2007 | Le et al. |
| 2007/0202104 A1 | 8/2007 | Banerjee et al. |
| 2007/0298040 A1 | 12/2007 | Le et al. |
| 2008/0025976 A1 | 1/2008 | Le et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0311043 A1 | 12/2008 | Hoffman et al. |
| 2009/0028794 A1 | 1/2009 | Medich et al. |
| 2009/0110679 A1 | 4/2009 | Li et al. |
| 2009/0123378 A1 | 5/2009 | Wong et al. |
| 2009/0226530 A1 | 9/2009 | Lassner et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0021451 A1 | 1/2010 | Wong |
| 2010/0040630 A1 | 2/2010 | Elden et al. |
| 2010/0278822 A1 | 11/2010 | Fraunhofer et al. |
| 2011/0171227 A1 | 7/2011 | Okun et al. |
| 2012/0014956 A1 | 1/2012 | Kupper et al. |
| 2012/0129185 A1 | 5/2012 | Maksymowych et al. |
| 2013/0122011 A1 | 5/2013 | Hoffman et al. |
| 2013/0243786 A1 | 9/2013 | Banerjee et al. |

FOREIGN PATENT DOCUMENTS

| | | |
|---|---|---|
| EP | 0212489 | 3/1987 |
| EP | 0351789 | 1/1990 |
| EP | 0366043 | 5/1990 |
| EP | 0492448 | 7/1992 |
| EP | 260 610 | 9/1993 |
| EP | 0614984 | 9/1994 |
| EP | 0659766 | 6/1995 |
| EP | 1174148 | 1/2002 |
| EP | 1254666 A1 | 11/2002 |
| HU | 211626 A9 | 12/1995 |
| JP | 11127882 | 5/1999 |
| JP | 2001-302542 | 10/2001 |
| WO | WO-91/02078 | 2/1991 |
| WO | WO-91/03553 A1 | 3/1991 |
| WO | WO-91/09967 A1 | 7/1991 |
| WO | WO-92/11383 | 7/1992 |
| WO | WO-92/16553 | 10/1992 |
| WO | WO-93/06213 | 4/1993 |
| WO | WO-93/11793 | 6/1993 |
| WO | WO-94/29347 | 12/1994 |
| WO | WO-95/23813 | 9/1995 |
| WO | WO-97/04801 | 2/1997 |
| WO | WO-97/29131 | 8/1997 |
| WO | WO-98/05357 | 2/1998 |
| WO | WO-98/22460 | 5/1998 |
| WO | WO-98/56418 | 6/1998 |
| WO | WO-00/51637 | 9/2000 |
| WO | WO-01/00229 | 1/2001 |
| WO | WO-01/37874 | 5/2001 |
| WO | WO-01/43773 | 6/2001 |
| WO | WO-01/47554 | 7/2001 |
| WO | WO-01/62272 | 8/2001 |
| WO | WO-01/94585 | 12/2001 |
| WO | WO-02/12502 | 2/2002 |
| WO | WO-02/096461 | 12/2002 |
| WO | WO-02/100330 | 12/2002 |
| WO | WO-2004/009776 A2 | 1/2004 |
| WO | WO-2004/037205 A2 | 5/2004 |
| WO | WO-2006/041970 | 4/2006 |

OTHER PUBLICATIONS

Barrera et al., "Effect of a Fully Human Anti-TNFa Monoclonal Antibody on the Local and Systemic Expression of TNFa and IL-113," Arthritis Rheum, 42(9):S75 (1999).

Baugh et al., "Mechanisms for modulating TNFa in immune and inflammatory disease," Current Opinion in Drug Discovery & Development, 4(5):635-650 (2001).

Bender et al., "Immunogenicity, efficacy and adverse events of adalimumab in RA patients," Rheumatol. Int, 27:269-274 (2007).

Biester et al., "Adalimumab in the therapy of uveitis in childhood," Br. J. Ophthalmology, 91(3):319-324 (2007).

Bodmer et al., "Preclinical review of anti-tumor necrosis factor monoclonal antibodies," Critical Care Medicine, 21(10):S441-S446 (1993).

Burmester et al., "Sustained Efficacy of Adalimumab Monotherapy for More than Four Years in DMARD-Refractory RA," Ann. Rheum. Dis., 62(1):192-3 (2003).

Chaudhari et al., "Efficacy and safety of infliximab monotherapy for plaque-type psoriasis: a randomized trial," Lancet, 357(9271):1842-7 (2001).

Corluy, "Clinical Response Compared to DAS28 and ACR-Response Criteria in Rheumatoid Arthritis Patients on Infliximab," EULAR, abstract (2002).

Emery et al., "Improvement in HAQ Disability in Rheumatoid Arthritis (RA) with Adalimumab (Humira ™) Based on Duration of Disease," Arthritis Rheum, 48(9):S313 (2003).

Enbrel (etanercept) Label, 2007.

Ettehadi et al., "Elevated tumor necrosis factor-alpha (TNF-a) biological activity in psoriatic skin lesions," Clin. Exp. Immunol, 96:146-151 (1994).

FDA approval of Humira (adalimumab): Prescribing information for Humira (adalimumab), Abbott Laboratories, North Chicago, IL, USA, Dec. 20, 2002, pp. 1-16.

Foster et al., "Secondary glaucoma in patients with juvenile rheumatoid arthritis-associated iridocyclitis," Acta Opthalmol. Scand, 78(5):576-579 (2000).

Genovese et al., "Adalimumab efficacy in patients with psoriatic arthritis who failed prior DMARD therapy," Ann Rheum Dis., 64(3):313 (2005).

(56) References Cited

OTHER PUBLICATIONS

Gordon et al., "Clinical Response to Adalimumab Treatment in Patients with Moderate to Severe psoriasis: Double-Blind, Randomized Controlled Trial and Open-Label Extension Study," J. Am. Acad. Derm., 55(1):598-606 (2006).
Goto et al., "Adalimumab," Medline AC NLM12510366 (2002).
Highlights of Humira Prescribing Information, Abbott Laboratories, North Chicago, IL, USA, pp. 1-70, updated Mar. 2011.
Highlights of Humira Prescribing Information, Abbott Laboratories, North Chicago, IL, USA, pp. 1-53, updated Mar. 2009.
Highlights of Humira Prescribing Information, Abbott Laboratories, North Chicago, IL, USA, updated Feb. 2008.
Honkanen et al., "Infliximab Treatment in the refractory chronic uveitis of juvenile idiopathic arthritis (JRA)," Arthritis & Rheumatism, 44:277-390, (2001) abstract #1438.
http://www.marketwatch.com/story/biogen-slumps-cdp-571-studyresults-miss-endpoint (Jul. 30, 2002).
Humira (Adalimumab) European Medicines Agency (EMA) Assessment Report (Jul. 24, 2008).
Humira (adalimumab). Data Sheet [online]. Abbott Laboratories, Dec. 20, 2002 [retrieved on Jun. 7, 2013]. Retrieved from the Internet: URL: www.fda.gov/downloads/Drugs/DevelopmentApprovalProcess/HowDrugsareDevelopedandApproved/ApprovalApplications/TherapeuticBiologicApplications/ucm092762.pdf.
Humira FDA approval letter for PsA, Oct. 3, 2005.
Humira Prescribing Information, Abbott Laboratories, North Chicago, IL, USA, pp. 1-33, Sep. 27, 2005.
Humira Prescribing Information, Abbott Laboratories, North Chicago, IL, USA, pp. 1-24, Jul. 30, 2004.
Imrie et al., "Biologics in the treatment of uveitis," Curr. Opin. Opthalmol., 18:481-486 (2007).
Iyer et al., "Etanercept for severe psoriasis and psoriatic arthritis: observations on combination therapy," Br. J. Dermatol, 146(1):118-21 (2002).
Janeway, "The structure of a typical antibody molecule," Immunobiology, 5 (2001).
Kalden et al., "Emerging role of anti-tumor necrosis factor therapy in rheumatic diseases," Arthritis Research, 4(2): S34-40 (2002).
Klippel et al., "A. Epidemiology, Pathology, and Pathogenesis," Primer on Rheumatic Diseases, 11:155 (1997).
Klippel et al., "A. Juvenile Rheumatoid Arthritis and Juvenile Spondyloarthropathies," Primer on Rheumatic Diseases, 11:393 (1997).
Klippel, et al., "Juvenile Idiopathic Arthritis C. Treatment and Assessment," Primer on Rheumatic Diseases, 13:154-162 (2008).
Lack and Stuard-Taylor, "Calculation of drug dosage and body surface area of children," Br. J. Anaesthes., 78:601-605 (1997).
Lorenz et al., "Technology evaluation: Adalimumab, Abbott Laboratories," Current Opinions in Molecular Therapeutics, 4(2): 185-190 (2002).
Mangge et al., "Therapeutic experience with infliximab in a patient with polyarticular juvenile idiopathic arthritis and uveitis," Rheumatol Int., 5:258-261 (2003).
Mansour et al., "Adalimumab in the therapy of uveitis in childhood," Br. J. Ophthalmol, 91:274-276 (2007).
Mease, "Adalimumab: an anti-TNF agent for the treatment of psoriatic arthritis," Expert Opin. Biol. Ther., 5(11):1491-1504 (2005).
Mease, "Tumour necrosis factor (TNF) in psoriatic arthritis: pathophysiology and treatment with TNF inhibitors," Ann Rheum Dis., 61:298-304 (2002).
Mussi et al., "Serum TNF-alpha levels correlate with disease severity and are reduced by effective therapy in plaque-type psoriasis," J Bil Reul Homeost Agents, 11(3):115-8 (1997).
Myers et al., "Juvenile arthritis and autoimmunity to type II collagen," Arthrit. Rheum., 8:1775-1781 (2001).
Neuner et al., "Cytokine release by peripheral blood mononuclear cells is affected by 8-methoxypsoralen plus UV-A," Photochem Photobiol., 59(2):182-188 (1994).

Ogilvie et al., "Treatment of psoriatic arthritis with antitumor necrosis factor-a antibody clears skin lesions of psoriasis resistant to treatment with methotrexate," British Journal of Dermatology, 144(3):587-589, (2001).
Oh et al., "Treatment with anti-tumor necrosis factor alpha (TNF-alpha) monoclonal antibody dramatically decreases the clinical activity of psoriasis lesions," Journal of the American Academy of Dermatology, 42(5 Pt 1):829-30 (2000).
Orthoclone OKT® 3 Sterile Solution (murumonab-CD3) product label (Mar. 2001).
Partsch et al., "Highly increased levels of tumor necrosis factor-alpha and other proinflammatory cytokines in psoriatic arthritis synovial fluid," J. Rheumatol., 24(3):518-23 (1997).
Rau et al., "Low dose prednisolone therapy (LDPT) retards radiographically detectable destruction in early rheumatoid arthritis—Preliminary results of a multicenter, randomized, parallel, double blind study," Z. Rheumatol., 59(2):II/90-II/96 (2000).
Reinhart et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," Crit. Care. Med., 24(5):733-742 (1996).
Remicade (infliximab) Product Label (Jun. 2002).
Ruperto et al., "A randomized, double-blind clinical trial of two doses of meloxicam compared with naproxen in children with juvenile idiopathic arthritis: short- and long-term efficacy and safety results," Arth. and Rheum., 52(2):563-72 (2005).
Sandborn et al., "CDP571, a humanised monoclonal antibody to tumour necrosis factor α, for moderate to severe Crohn's disease: a randomized, double blind, placebo controlled trial," Gut, 53:1485-1491 (2004).
Sandborn et al., "Etanercept for Active Crohn's Disease: A Randomized, Double-blind, Placebo-Controlled Trial," Gastroenterol, 121:1088-1094 (2001).
Schattenkirchner et al, "Efficacy and Tolerability of Weekly Subcutaneous Injections of the Fully Human Anti-TNF-Antibody D2E7 in Patients with Rheumatoid Arthritis—Results of a Phase I Study," Arthritis and Rheumatism, 41(9):S57 (1998).
Schopf et al., "Treatment of psoriasis with the chimeric monoclonal antibody against tumor necrosis factor a, infliximab," J. Am. Acad. Dermatol, 46(6):886-91 (2002).
Schwartzman et al., "Do anti-TNF agents have equal efficacy in patients with rheumatoid arthritis?" Arth Res Ther., 6(2):S3-S11 (2004).
Shealy et al., "Characterization of golimumab, a human monoclonal antibody specific for human tumor necrosis factor alpha," mAbs, 2(4):1-12 (2010).
Smith, "Ibuprofen in psoriatic arthritis," Arthritis Rheum., 23(8):961-962 (1980).
Spencer-Green, "Etanercept (Enbrel): update on therapeutic use," Ann Rheum Dis., 59(1):i46-i49 (2000).
Stolzenberg et al., "Korpermabe bei kindern und Jugenlichen in Deutschland," Bundesgesundheitsbl, 50:659-669 (2007).
Thomson, "Abbott seeks U.S. and E.U. approval for D2E7 in rheumatoid arthritis," Reuters Drug News, Apr. 10, 2002, Retrieved from https ://integrity.thomsonpharma.coml/integrity/xmlxsl/pk_ref_list.xml_show_ficha_ref?p_ref id=662437.
Visvanthan et al., "The effects of infliximab plus methotrexate therapy on the modulation of inflammatory disease markers in patients with juvenile rheumatoid arthritis," Arthritis & Rheumatism, 52(S):s86 (2005).
Wollina et al., "Treatment of recalcitrant psoriatic arthritis with anti-tumor necrosis factor-alpha antibody," J. Eur. Acad. Dermatology and Venereology, 16(2):127-129 (2002).
Yamauchi et al., "Adalimubab in the Management of Hidradenitis Suppurativa," J Am Acad. Deam., AB41:P504 (2007).
Abraham et al., "Efficacy and Safety of Monoclonal Antibody to Human Tumor Necrosis Factor a in Patients with Sepsis Syndrome," JAMA, 273(12): 934-941 (1995).
Alexander et al., "Elevated Levels of Proinflammatory Cytokines in the Seman of Patients With Chronic Prostatitis/Chronic Pelvic Pain Syndrome," Urology, 52:744 (1998).

(56) References Cited

OTHER PUBLICATIONS

Arthur et al.,"Safety of self-injection of gold and methotrexate," J Rheumatol. 26(2):302-5 (1999).
Asakawa et al., "Effects of Cernitin Pollen-Extract (Cernilton) on Inflammatory Cytokines in Sex-Hormone Induced Nonbacterial Prostatitis Rats," Hinyokika Kiyo, 47:459-465 (2001).
Atlas Study Group., "Adalimumab therapy results in significant reduction of signs and symptoms in subjects with ankylosing spondylitis: the ATLAS trial," Arthritis & Rheumatism, 52(9):S281 (2005).
Aulton, "Biopharmaceutical Principles of Drug Delivery," Pharmaceutics: The Science of Dosage Form Design, 275-288 (2001).
Awni et al., "Steady-State Pharmacokinetics (PK) of Adalimumab (HUMIRA1M, Abbott) Following 40 mg Subcutaneous (sc) Injection Every Other Week (eow) in Rheumatoid Arthritis (RA) Patients with and without Methotrexate (MTX) Background Therapy," Arthritis Rheum, 48(9):S140 (2003).
Bansback et al., "The Cost Effectiveness of Adalimumab (Humira™, Abbott) in the Treatment of Patients with Moderate to Severe Rheumatoid Arthritis (RA)," Arthritis Rheum, 48(9):S611 (2003).
Barbuto et al., "Production of Neutralizing Antibodies to Tumor Necrosis Factor by Human Tumor-Infiltrating B Lymphocytes," Proc. Am. Assoc. Cancer Res, 34(487) Abstr. 2904 (1993).
Barrera et al., "Drug survival, efficacy and toxicity of monotherapy with a fully human antitumournecrosis with a fully human antitumour necrosis factor-a antibody compared with methotrexate in long-standing rheumatoid arthritis," Rheumatology, 41:430-439 (2002).
Barrera et al., "Effects of treatment with a fully human anti-tumour necrosis factor a monoclonal antibody on the local and systemic homeostasis of interleukin 1 and TNFa in patients with rheumatoid arthritis," Ann. Rheum Dis., 60:660-669 (2001).
Beers et al., "Juvenile rheumatoid arthritis," The Merck Manual of Diagnosis and Therapy, 17(270):2402-2403 (1999).
Bendtzen et al., "Auto-antibodies to IL-1a and TNFa in Normal Individuals and in Infectious and Immunoinflammatory Disorders," The Physiological and Pathological Effects of Cytokines, 447-452 (1990).
Billiau et al., "Infliximab for systemic onset juvenile idiopathic arthritis: experience in 3 children," Journal of Rheumatology, 29(5):1111-1114 (2002).
Bloom et al., "Development of diabetes mellitus during etanercept therapy in a child with systemic-onset juvenile rheumatoid arthritis," Arthritis & Rheum, 43:2606-2608 (2000).
Boekstegers et al., "Repeated administration of a F(ab')2 fragment of an anti-tumor necrosis factor alpha monoclonal antibody in patients with severe sepsis: effects on the cardiovascular system and cytokine levels," Shock, 1(4):237-245 (1994).
Bombardier et al., "Pattern of DMARD use in a North American Cohort of Patients with Early Rheumatoid Arthritis (RA) (SONORA)," Arthritis Rheum, 46(9):S344 (2002).
Borg et al., "Biologic treatments in rheumatoid arthritis and juvenile idiopathic arthritis," Malta Medical Journal, 18(1):20-24 (2006).
Borigini et al., "Innovative Treatment Approaches for rheumatoid arthritis. Combination Therapy," Bailliere's Clinical Rheumatology, 9(4):689-710 (1995).
Boulos et al., "Pharmacological treatment of ankylosing spondylitis: a systematic review," Drugs, 65(15):2111-2127 (2005).
Boyle et al., "A Novel Monoclonal Human IgM Autoantibody which Binds Recombinant Human and Mouse Tumor Necrosis Factor—a," Cell. Immunol, 152:556-68 (1993).
Boyle et al., "The B5 Monoclonal Human Autoantibody Binds to Cell Surface TNFa on Human Lymphoid Cells and Cell Lines and Appears to Recognize a Novel Epitope," Cell. Immunol., 152:569-81 (1993).
Braun et al., "Biologic therapies in the spondyloarthritis: new opportunities, new challenges," Curr Opin Rheumatol, 15(4):394-407 (2003).

Breedvald et al., "The efficacy and safety of Adalimunab (Humira((R))) plus Methotrexate vs. Adalimumab alone or methotrexate alone in the early treatment of rheumatoid arthritis (RA): 1- and 2-year results of the premier study," Annals of the Rheumatic Diseases, 64(3): 60 (2005).
Breedveld et al., "Sustained Efficacy Over 4 Years with Adalimumab in Patients with Active Rheumatoid Arthritis," Ann. Rheum. Dis, 62(1):169 (2003).
Breedveld et al., "Sustained Efficacy over 5 Years with Adalimumab (HUMIRA1M) in Patients with Active Rheumatoid Arthritis," Arthritis Rheum, 48(9):S118 (2003).
Breedveld et al., "The Fully Human Anti-TNF Antibody Adalimumab (D2E7) in Combination with Methotrexate (MTX) in the Treatment of Active Rheumatoid Arthritis: Results of a 2-Year Study," EULAR, Prague, Czech Republic (2001).
Breedveld et al., "The Long-term Efficacy and Safety of Adalimumab (D2E7), the Fully Human Anti-TNF Monoclonal Antibody, in Combination with Methotrexate in the Treatment of Rheumatoid Arthritis: Results of a 2-Year Study," JCR, 8(3):S46 (2002).
Brekke et al., "Therapeutic Antibodies for Human Diseases at the Dawn of the Twenty-first Century," Nat Rev Drug Discov., 2(3):240 (2003).
Bresnihan et al., "The safety and efficacy of interleukin-1 receptor antagonist in the treatment of rheumatoid arthritis," Semin Arthritis Rheum, 30(5 Suppl 2):17-20 (2001).
Brisby et al., "Proinflammatory cytokines in cerebrospinal fluid and serum in patients with disc herniation and sciatica", Eur Spine J., 11:62-66 (2002).
Burmester et al., "Effect of Dose Interruptions on the Efficacy and Safety of Adalimumab in Patients with RA," Ann. Rheum. Dis., 62(1):192 (2003).
Burmester et al., "Long-Term Efficacy and Safety of Adalimumab (D2E7) Monotherapy in Patients With DMARD-Refractory Rheumatoid Arthritis—Results From a 2-Year Study," Arthritis Rheum, 46(9):S537 (2002).
Butler et al., "Modulation of proinflammatory cytokine release in rheumatoid synovial membrane cell cultures. Comparison of monoclonal anti TNF-alpha antibody with the IL-1 receptor antagonist," Eur. Cytokine Netw., 6(4):225-30 (1995).
Carrasco et al. Ped. Drugs 6:137-146 (2004).
Case, "Old and New Drugs Used in Rheumatoid Arthritis: A Historical Perspective," American Journal of Therapeutics, 8:163-179 (2001).
Casset et al., "A peptide mimetic of an anti-CD4 monoclonal antibody by rational design," Biochemical and Biophysical Research Communications, 307:198-205 (2003).
Cate et al., "Etanercept in four children with therapy-resistant systemic juvenile idiopathic arthritis," Paediatric Rheumatology, 41:228-229 (2002).
Cavagna et al., "Infliximab in the treatment of adult Still's disease refractory to conventional therapy," Clin Exp Rheumatol, 19(3):329-332 (2001).
Chartash et al., "Adalimumab Improves Fatigue in Patients with Active Rheumatoid Arthritis," Ann. Rheum. Dis., 62(1):349 (2003).
Chikanza, "Juvenile rheumatoid arthritis: therapeutic perspectives," Pediatric Drugs 4(5):335-348 (2002).
Chow et al., "Effect of monoclonal antibody on human tumor necrosis factor (TNF MAb) on NFa, IL-113. and IL-61evels in patients with sepsis syndrome," Clinical Research, 42(2): 299A (1994).
Cleland et al., "A specific molar ratio of stabilizer to protein is required for storage stability of a lyophilized monoclonal antibody," Journal of Pharm. Sciences, 90(3):310-321 (2001).
Clinical Trial NCT0029042, "A Randomized Double Blind Controlled Intra-Patient Dose Escalation Phase II Trial of Infliximab in Pediatric Patients With Refractory Juvenile Rheumatoid Arthritis" (Feb. 28, 2007). Retrieved from the Internet:URL:http://clinicaltrials.govjarchivejNCTO0029042/2007 02 28 [retrieved on Oct. 28, 2011].
Cohen et al., "Intersept: An international, multicenter, placebo-controlled trial of monoclonal antibody to human tumor necrosis factor-a in patients with sepsis," Crit Care Med., 24(9):1431-1440 (1996).
Cox et al., "A directory of human germ-line V segments reveals a strong bias in their usage," Eur. J. Immunol., 24(2):827-36 (1994).

(56) References Cited

OTHER PUBLICATIONS

Cummins et al., "A systematic review of effectiveness and economic evaluation of new drug treatments for juvenile idiopathic arthritis: etanercept," Health Technology Assessment, 6(17) (2002).
Davis et al., "Major clinical response and partial remission in ankylosing spondylitis subjects treated with adalimumab: the ATLAS trial," Arthritis & Rheumatism, 52(9):S208-S209 (2005).
Davis, "Understanding the role of tumor necrosis factor inhibition in ankylosing spondylitis," Seminars in Arthritis and Rheumatism, 34(4):668-677 (2005).
den Broeder et al., "A Single Dose, Placebo Controlled Study of the Fully Human Anti-Tumor Necrosis Factor-a Antibody Adalimumab (D2E7) in Patients with Rheumatoid Arthritis," The Journal of Rheumatology, 29(11): 2288-2298 (2002).
den Broeder et al., "Long term anti-tumour necrosis factor a monotherapy in rheumatoid arthritis: effect on radiological course and prognostic value of markers of cartilage turnover and endothelial activation," Ann. Rheum. Dis., 61:311-318 (2002).
den Broeder et al., "The Effect of D2E7, a new human anti-TNFa monoclonal antibody, on the oxidative burst of PMN in patients with RA," Arthritis and Rheumatism, 41(9):S57 (1998).
Department of Surgery, University of Toronto, Annual Report (1998-1999) found online at http://www.surQ.med.utoronto.ca/AnnRep/AR98 99/index.html.
Doring et al., "Identification and Characterization of a TN Fa Antagonist Derived From a Monoclonal Antibody," Mol. Immunol., 31:1059-1067 (1994).
Efthimiou et al., "Role of biological agents in immune-mediated inflammatory diseases," Southern Medical Journal, Southern Medical Association, 98(2):192-204 (2005).
Egan et al., "A randomized, single-blind, pharmacokinetic and dose response study of subcutaneous methotrexate, 15 and 25 MG/week, for refractory ulcerative colitis and Crohn's Disease," Gastroenterology, 114(4):G3978 (1998).
Eisermann et al., "Tumor necrosis factor in peritoneal fluid of women undergoing laparoscopic surgery," Fertility and Sterility, 50:573 (1988).
Elliott et al., "Suppression of fever and the acute-phase response in a patient with juvenile chronic arthritis treated with monoclonal antibody to tumour necrosis factor-alpha (cA2)," British Journal of Rheumatology, 36(5): 589-593 (1997).
Elliott et al., "Treatment of rheumatoid arthritis with chimeric monoclonal antibodies to tumor necrosis factor a," Arthritis & Rheumatism, 36(12):1681-90 (1993).
Emery et al., "Changes in PRO-MMP-1 in Relation to Standard Measures of Disease Activity Over a 6 Month Treatment Period with Adalimumab (D2E7) in Rheumatoid Arthritis," Arthritis & Rheumatism, 44(9):S215 (2001).
Emery, et al., "Targeted therapies in rheumatoid arthritis: the need for action," Rheumatology, 38(10):911-2 (1999).
Feldmann et al., "Anti-TNF Therapy of Rheumatoid Arthritis: What Have We Learned," Annu. Rev. Immunol., 19:163-196 (2001).
Figini et al., "In Vitro Assembly of Repertoires of Antibody Chains on the Surface of Phage by Renaturation," J. Mol. Biol., 239:68-78 (1994).
Fomsgaard et al., "Auto-antibodies to Tumour Necrosis Factor a in Healthy Humans and Patients with Inflammatory Diseases and Gram-Negative Bacterial Infections," Scand. J. Immunol, 30:219-23 (1989).
Foote et al., "Antibody Framework Residues Affecting the Conformation of the Hypervariable Loops," J. Mol. Biol., 224:487-499 (1992).
Fox et al., "Sjogren's Syndrome," Arthritis and Rheumatism, 29:577-85 (1986).
Furst et al., "Adalimumab, a Fully Human Anti-Tumor Necrosis Factor-a Monoclonal Antibody, and Concomitant Standard Antirheumatic Therapy for the Treatment of Rheumatoid Arthritis: Results of STAR (Safety Trial of Adalimumab in Rheumatoid Arthritis)," The Journal of Rheumatology, 30(12):2563-2571 (2003).
Furst et al., "Improvement of the Individual ACR Components in ACR20 Responders in an Adalimumab (Humira™) RA Clinical Trial," Arthritis Rheum, 48(9):S106 (2003).
Furst et al., "Safety and Efficacy of Adalimumab (D2E7), a Fully Human Anti-TNF-a Monoclonal Antibody, Given in Combination with Standard Antirheumatic Therapy: Safety Trial of Adalimumab in Rheumatoid Arthritis," Arthritis Rheum., 46(9):S572 (2002).
Furst et al., "TNF Blockade by the Fully Human Monoclonal Antibody Adalimumab (D2E7), in the Armada Trial Results in Decreases in Serum Matrix Metalloproteinase (MMP) Levels Along with Impressive Clinical Improvement in Refractory RA Patients," Arthritis Rheum., 44(9):S215 (2001).
Gerloni et al., "Infliximab in the treatment of persistently active refractory juvenile idiopathic (chronic) arthritis: A short-term pilot study," Arthritis & Rheumatism 43(9): S256, abstract #1139 (2000).
Giannini et al., "Preliminary definition of improvement in juvenile arthritis," Arthritis & Rheumatism, 40:1202 (1997).
Goto et al., "Adalimumab," Nippon Rinsho (Japanese Journal of Clinical Medicine ), 60(12): 2384-2389 (2002).
Granneman et al., "Pharmacokinetic/Pharmacodynamic (PKIPD) Relationships of Adalimumab (Humira TM, Abbott) in Rheumatoid Arthritis (RA) Patients during Phase II/III Clinical Trials," Arthritis. Rheum., 48(9):S140 (2003).
Griffiths et al. "Human anti-self antibodies with high specificity from phage display libraries," The EMBO J., 12(2):725-34 (1993).
Grom et al., "Patterns of Expression of Tumor Necrosis Factor a, Tumor Necrosis Factora, and Their Receptors in Synovia of Patients with Juvenile Rheumatoid Arthritis and Juvenile Spondylarthropathy," Arthritis & Rheumatism, 39(10):1703-1710 (1996).
Haibel et al., "Adalimumab in the treatment of active ankylosing spondylitis: results of an open label," 52-week trial Annals of the Rheumatic Diseases, 64(3):316 (2005).
Haibel et al., "Adalimumab reduces spinal symptoms in active ankylosing spondylitis: clinical and magnetic resonance imaging results of a fifty-two-week open-label trial Arthritis and Rheumatism," 54(2):678-681 (2006).
Halme, "Release of tumor necrosis factor-a by a human peritoneal macrophages in vivo and in vitro," Am J Obstet Gynecol, 161:1718 (1989).
Hannes, "CD147," Protein Reviews on the Web, http://mpr.nci.nih.gov/prow/guide/1397527348_g.htm (1999).
Harris et al., "Expression of proinflammatory Genes During Estrogen-Induced Inflammation of the Rat Prostate," Prostate, 44:19-25 (2000).
Hashkes et al., "Medical treatment of juvenile idiopathic arthritis," J. Am. Med. Assoc., 294(13):1671-1684 (2005).
Hawkins et al., "Selection of Phage Antibodies by Binding Affinity Mimicking Affinity Maturation," J. Mol. Biol., 226:889-896 (1992).
Hillgren et al., "Protection mechanism of Tween 80 during freeze-thawing of a model protein," LDH International Journal of Pharmaceutics, 237(1-2): 57-69 (2002).
Holler et al., "Modulation of Acute Graft-Versus-Host Disease After Allogeneic Bone Marrow Transplantation by Tumor Necrosis Factor a (TN Fa) Release in the Course of Pretransplant Conditioning: Role of Conditioning Regimens and Prophylactic Application of a Monoclonal Antibody Neutralizing Human TNFa (MAK 195F)," Blood, 86(3):890-899 (1995).
Holliger et al., "Engineered antibody fragments and the rise of single domains," Nature Biotechnology, 23(9): 1126-1136 (2005).
Holt et al., "Domain Antibodies: Proteins for Therapy," Trends in Biotech, 21(11): 484-490 (2003).
Hoogenboom et al., "Converting rodent into human antibodies by guided selection," Antibody Engineering, 8:169-185 (1996).
Horneff, "Stellenwert der neuen Biologicals und Zytokinantagonisten in der Therapie der juvenilen idiopathischen Arthritis (JIA) [Importance of the new biologicals and cytokine antagonists in the treatment of juvenile idiopathic arthritis (JIA)]," Zeitschrift fur Rheumatologie, 64(5):317-26 (2005).
Humira (adalimumab) Package Insert. Dec. 20, 2002. Retrieved from the Internet Dec. 11, 2009; <http://www.fda.gov/cder/foi/label/2002/adalabb1231 021b.pdf>; p. 1-3, 6.

(56) References Cited

OTHER PUBLICATIONS

Humira, Highlights of Prescribing Information, Abbott Laboratories, North Chicago, IL, USA, pp. 1-56, Nov. 2009.
Huse et al., "Generation of a large combinatorial library of the immunoglobulin repertoire in phage lambda," Science, 246:1275-81 (1989).
International Preliminary Examination Report for PCT/US2003/022566.
Janeway, "The protein products of MHC class I and class II genes are highly polymorphic," Immunobiology (3rd Edition) 4:24-4:30 (1997).
Jespers et al., "Guiding the Selection of Human Antibodies from Phage Display Repertoires to a Single Epitope of an Antigen," Bio/Technology, 12:899-903 (1994).
Johnson et al., "Etanercept in Juvenile Rheumatoid Arthritis," Annals Pharmacotherapy, 35:464-471 (2001).
Kanakoudi-Tsakalidou et al., "Influenza vaccination in children with chronic rheumatic diseases and long-term immunosuppressive therapy," Clinical and Experimental Rheumatology, 19:589-594 (2001).
Katsanos, et al., "Axillary hidradenitis suppurativa successfully treated with infliximab in a Crohn's disease patient," AJG 97:2155-2156 (2002).
Kavanaugh et al., "Immune Response is Not Affected by Adalimumab Therapy," Ann. Rheum. Dis., 62(1): 169 (2003).
Kavanaugh et al., "The Armada Trial: 12-Month Efficacy and Safety of Combination Therapy with Adalimumab (D2E7), the First Fully Human Anti-TNF Monoclonal Antibody, and Methotrexate (MTX) in Patients with Active Rheumatoid Arthritis," Ann. Rheum. Dis., 61(1):S168 (2002).
Kavanaugh et al., "Treatment with Adalimumab (D2E7) does not Affect Normal Immune Responsiveness," Arthritis Rheum., 46(9):S132 (2002).
Kaymakcalan et al., "Comparison of Adalimumab (D2E7), Infliximab, and Etanercept in the Prevention of Polyarthritis in the Transgenic Murine Model of Rheumatoid Arthritis," Arthritis, Rheum., 46(9):S304 (2002).
Kaymakcalan et al., "Murine Model for Assessing Adalimumab, Infliximab, and Etanercept to Prevent Polyarthritis," Ann. Rheum. Dis., 62(1):136-7 (2003).
Kempeni, "Preliminary Results of early clinical trials with the fully human anti-TNFα monoclonal antibody D2E7," Ann. Rheum. Dis., 58(1):170-172 (1999).
Kempeni, "Update on D2E7: a fully human anti-tumour necrosis factor a monoclonal antibody," Ann. Rheum. Dis., 59(1):144-145 (2000).
Keystone et al., "Adalimumab Inhibits the Progression of Structural Joint Damage in Patients with Active RA," Ann. Rheum. Dis., 62(1):64-5 (2003).
Keystone et al., "Efficacy and Safety of Adalimumab (D2E7), the Fully Human Anti-TNF Monoclonal Antibody, in MTX Partial Responders: Results of the 24-week ARMADA Trial," JCR: Journal of Clinical Rheumatology, 8(3):S69 (2002).
Keystone et al., "Subgroup Analysis of Radiographic Progression in RA Patients with Moderate Disease Treated with Adalimumab (Humira®)," Ann. Rheum. Dis., 62(1):169 (2003).
Keystone et al., "Sustained Radiographic Inhibition with Adalimumab (HUMIRAr) over 2 years in Patients with Long Standing Rheumatoid Arthritis (RA)," Arthritis Rheum., 48(9):S315 (2003).
Keystone et al., "The Armada Trial: A Double-Blind Placebo Controlled Trial of the Fully Human Anti-TNF Monoclonal Antibody, Adalimumab (D2E7), in Patients with Active RA on Methotrexate (MTX)," Arthritis & Rheumatism, 44(9):S213 (2001).
Keystone et al., "The Fully Human Anti-TNF Monoclonal Antibody, Adalimumab (D2E7), Dose Ranging Study: The 24-Week Clinical Results in Patients with Active RA on Methotrexate Therapy (The ARMADA Trial)," (EULAR), Prague, Czech Republic, (2001).

Keystone, et al., "Response to Adalimumab in Patients with Early Versus Late Rheumatoid Arthritis (RA)," Ann. Rheum. Dis., 62(1):170 (2003).
Kietz et al., "Clinical response to etanercept in polyarticular course juvenile rheumatoid arthritis," J. Rheumatology, 28(2):360-362 (2001).
Kietz et al., "Therapeutic use of etanercept in polyarticular course juvenile idiopathic arthritis over a two year period," Ann. Rheum. Dis., 61(2):171-3 (2002).
Koski et al., "Tumor necrosis factor-alpha and receptors for it in labial salivary glands in Sjogren's syndrome," Clin Exp Rheumatol., 19:131 (2001).
Kraetsch et al., "Successful treatment of a small cohort of patients with adult onset of Still's disease with infliximab: first experiences," Annals of the Rheumatic Diseases, 60(3):iii55-iii57 (2001).
Kremer, "Rational Use of New and Existing Disease-Modifying Agents in Rheumatoid Arthritis," Ann. Intern. Med., 134:695-706 (2001).
Landenne et al., "Infliximab or etantercept in the treatment of children with refractory juvenile idiopathic arthritis: an open label study," Ann. Rhem. Dis., 62(3):245-247 (2003).
Landenne et al., "Infliximab vs Etanercept in the treatment of severe juvenile chronic arthritis," Arthritis & Rheumatism, 43(1): S381 abstract #1888 (2001).
Lerner et al., "Antibodies without immunization," Science, 258:1313-14 (1992).
Leusch et al., "Failure to demonstrate TNFa-specific autoantibodies in human sera by ELISA and Western blot," J. Immunol Methods, 139:145-47 (1991).
Lewis et al., "Use of alanine scanning mutagenesis to improve the affinity of an anti gp120 (HIV) antibody," J. Cell. Biochem., 18D:215 (1994).
Lipsky et al., "Infliximab and Methotrexate in the Treatment of Rheumatoid Arthritis," The New England Journal of Medicine, 343(22):1594-1602 (2000).
Lipsy, "Etanercept and its implications for managed care," Am J of Managed Care, 8(6):S194-S200 (2002).
Lorenz et al., "Perspectives for TNF-alpha-targeting therapies," Arthritis Research, 4(3):S17-24 (2002).
Lovell et al., "Etanercept in children with polyarticular juvenile rheumatoid arthritis," NEJM 342:763-769, (2000).
Lovell et al., "Long-Term Efficacy and Safety of Adalimumab in Children with Juvenile Rheumatoid Arthritis (JRA): 48-Week Results.," Arthritis Rheum 54(9):S303 (2006) [abstract 659].
Lovell et al., "Preliminary data from the study of adalimumab in children with Juvenile Idiopathic Arthritis," Arthritis & Rheumatism, 50(1096): S436-S437 (2004).
Lovell "Biologic agents for the treatment of juvenile rheumatoid arthritis: Current status," Pediatric Drugs, 6(3):137-146 (2004).
Low et al., "Mimicking Somatic Hypermutation: Affinity Maturation of Antibodies Displayed on Bacteriophage Using a Bacterial Mutator Strain," J. Mol. Biol., 260:359-368 (1996).
Low, thesis extract, Cambridge University (1996).
Luc Mathieu et al., "Patients without biological inflammation are responders to anti-TNF-alpha in axial ankylosing spondylitis," Arthritis & Rheumatism, 52(9):S216 (2005).
M03-606 Study Grp., "Efficacy of adalimumab in active ankylosing spondylitis (AS): results of the Canadian AS study Arthritis & Rheumatism," 52(9):S217 (2005).
MacCallum et al., "Antibody-antigen Interactions: Contact Analysis and Binding Site Topography," J. Mol. Biol., 262:732-745 (1996).
MacDonald et al., "Tumor necrosis factor-alpha and interferon-gamma production measured at the single cell level in normal and inflamed human intestine," Clin. Exp. Immunol., 81:301-305 (1990).
Machold et al., "Adalimumab—a new TNF-a antibody for treatment of inflammatory joint disease," Expert Opin. Biol. Ther., 3(2):351-360 (2003).
Maini et al., "Infliximab (chimeric anti-tumour necrosis factor a monoclonal antibody) versus placebo in rheumatoid arthritis patients receiving concomitant methotrexate: a randomised phase III trial," The Lancet, 354:1932-39 (1999).
Mangge et al., "Serum cytokines in juvenile rheumatoid arthritis," Arthritis Rheum. 8:211 (1995).

(56) References Cited

OTHER PUBLICATIONS

Marks et al., "By-Passing Immunization: Building High Affinity Human Antibodies by Chain Shuffling," Nature Biotechnology, 10:779-783 (1992).
Marks et al., "By-passing immunization: Human antibodies from V-gene libraries displayed on phage," J.Mol. Biol., 222:581-97 (1991).
Martinez et al., "Hidradenitis Suppurativa and Crohn's disease: Response to Treatment with Infliximab," Inflammatory Bowel Diseases, 7(4):323-326 (2001).
Martini et al., "Juvenile idiopathic arthritis: current and future treatment options," Expert Opinion on Pharmacotherapy, 7(4):387-399 (2006).
Marzi et al., "Effect of anti-tumor necrosis factor a on leukocyte adhesion in the liver after hemorrhagic shock: An intravital microscopic study in the rat," Shock, 3(1): 27-33 (1995).
Massarotti et al., "Treatment Patterns in Early-onset Rheumatoid Arthritis (RA): Results from the Sonora Study," Ann. Rheum. Dis., 61(1):S93 (2002).
Medynski, "Phage Display: All Dressed Up and Ready to Role," Bio/Technology, 12:1134-1136 (1994).
Mishra et al., "Histone deacetylase inhibitors modulate renal disease in the MRL-Ipr/Ipr mouse," J Clin Invest., 111(4):539-552 (2003).
Moller et al., "Monoclonal antibodies to human tumor necrosis factor a: in vitro and vivo application," Cytokine, 2(3):162-69 (1990).
Mori et al., "Peritoneal fluid interleukin-1/b and tumor necrosis factor in patients with benign gynecologic disease," Am J Reprod Immunol, 26:62 (1991).
Nadler et al., "11-1 Band TN F-a in prostatic secretions are indicators in the evaluation of men with chronic prostatitis," Journal Urology, 164:214 (2000).
National Institutes of Health definition of the term "dose" nlm.nih.Qov/medlineplus/mplusdictionary.html (2009).
Nilsson, "Antibody engineering," Current Opinion in Structural Biology, 5:450-456 (1995).
Oh et al., "The potential angiogenic role of macrophages in the formation of choroidal neovascular membranes," Invest Ophthalmol Visual Sci, 40:1891 (1999).
Orhan et al., "Seminal plasma cytokine levels in the diagnosis of chronic pelvic pain syndrome," Int J Urol, 8:495 (2001).
Osbourn et al., "From rodent reagents to human therapeutics using antibody guided selection," Methods, 36:61-68 (2005).
Overton et al., "Peritoneal fluid cytokines and the relationship with endometrosis and pain," Hum Reprod, 11:380 (1996).
Ozaktay et al., "Dorsal root sensitivity to interleukin-1 beta, interleukin-6 and tumor necrosis factor in rats," Eur Spine Journal, 11:467 (2002).
Paul, "Immunogenicity and Antigen Structure," Fundamental Immunology, 3(242):292-295 (1993).
Paulus et al., "Relative contributions of the components of the American College of Rheumatology 20% criteria for improvement to responder status in patients with early seropositive rheumatoid arthritis," Arthritis & Rheumatism; 43(12): 2743-2750 (2000).
Pincus et al., "Combination Therapy with Multiple Disease-Modifying Antirheumatic Drugs in Rheumatoid Arthritis: A Preventive Strategy," Ann. Intern. Med., 131:768-774 (1999).
Prahalad et al., "Etanercept in the treatment of macrophage activation syndrome," J. Rhematol., 28:2120-2124 (2001).
Prescribing Information for Humira (adalimumab) Injection, Solution for Subcutaneous use Initial U.S. Approval: 2002 (Updated Mar. 2009).
Queen et al., "A humanized antibody that binds to the interteukin 2 receptor," Proc. Natl. Acad. Sci. USA, 86:10029-10033 (1989).
Rader et al., "A phage display approach to rapid antibody humanization: Designed combinatorial V gene libraries," Proc Natl Acad Sci USA, 95:8910-8915 (1998).
Rau et al., "2.5-Year Treatment Results with Adalimumab (D2E7), the First Fully Human Anti-TNF Monoclonal Antibody, in Combination with Methotrexate in Active Rheumatoid Arthritis," Ann. Rheum. Dis., 61(1):S55 (2002).
Rau et al., "Adalimumab Inhibits Radiographic Disease Progression in Long-Standing, Rapidly Progressive Rheumatoid Arthritis," Ann. Rheum. Dis., 62(1):191 (2003).
Rau et al., "Combination therapy with the human anti-TNF antibody D2E7 and methotrexate in active chronic polyarthritis," Z. Rheumatol., 58(1): 1/35, F20 (1999).
Rau et al., "Effect and compatibility of repeated intravenous doses of the human anti-TNF antibody D2E7 in patients with chronic polyarthritis," Z. Rheumatol., 58(1):1/41, P12 (1999).
Rau et al., "Erfahrungen mit D2E7," Akt. Rheumatol., 25:83-88 (2000).
Rau et al., "Long-term efficacy and tolerability of multiple I.V. doses of the fully human Anti-TNF-Antibody D2E7 in patients with Rheumatoid Arthritis," Arthritis & Rheumatism, 41(137):S55 (1998).
Rau et al., "Long-term Treatment with the Fully Human Anti-TNF-Antibody D2E7 Slows Radio-graphic Disease Progression in Rheumatoid Arthritis," Arthritis and Rheumatism, 42(9):S400 (1999).
Rau, "Adalimumab (a fully human anti-tumour necrosis factor a monoclonal antibody) in the treatment of active rheumatoid arthritis: the initial results of five trials," Ann. Rheum. Dis., 61(2):ii70-ii73 (2002).
Rau, "Experiments with D2E7," Z. Rheumatol., 58(1):1-21, S51 (1999).
Rau, "Long-Term treatment with the fully human anti-TNF antibody D2E7 in rheumatoid arthritis—Effects on synovitis, PRO-MMPs and radiographic disease progression," Ann Rheum Dis., 59(1):S400 (2000).
Rau, "Long-Term Treatment with the Fully Human Anti-TNF-Antibody D2E7 Slows Radiographic Disease Progression in Rheumatoid Arthritis," APLAR, May 21-26, 2000, Beijing, China, 44 (2000).
Rau, et al., "Treatment with Adalimumab (D2E7), the Fully Human Anti-TNF Monoclonal Antibody, Slows Radiographic Disease Progression in Rheumatoid Arthritis: Results of a 12-Month Study," J. Clin. Rheum., 8:S78 (2002).
Reilly et al., "Use of genetic knockouts to modulate disease expression in a murine model of lupus, MRUipr mice," Immunologic Research, 25(2):143-153 (2002).
Reinhart et al., "Assessment of the safety and efficacy of the monoclonal anti-tumor necrosis factor antibody-fragment, MAK 195F, in patients with sepsis and septic shock: a multicenter, randomized, placebo-controlled, dose-ranging study," Crit. Care Med, 24(5):1608 (1996) (abstract).
Revicki et al., "Treatment with Adalimumab (D2E7), a Fully Human Anti-TNF Monoclonal Antibody, Improves Physical Function, Vitality, and Mental Health While Reducing Bodily Pain in Patients with Active Rheumatoid Arthritis (RA)," Arthritis Rheum., 46(9):S537 (2002).
Riechmann et al., "Phage Display and Selection of a Site-Directed Randomized Single-Chain Antibody Fv Fragment for Its Affinity Improvement," Biochemistry, 32:8848-8855 (1993).
Rinehart-Kim et al., "Alterations in the Gene Expression Profile of MCF-7 Breast Tumor Cells in Response to c-Jun," Int. J. Cancer, 88:180-190 (2000).
Rudikoff et al., "Single amino acid substitution altering antigen-binding specificity," Proc. Natl. Acad. Sci. USA, 79(6):1979-1983 (1982).
Ruperto et al. Arthr. Rheum 56:3096-3106 (2007).
Ruperto, "48-Week Data From the Study of Adalimumab in Children With Juvenile Rheumatoid Arthritis (JRA)," Ann. Rheum. Dis., 65(2):56 (2006).
Salfeld et al., "Generation of Fully Human Anti-TNF Antibody D2E7," Arthritis Rheum., 41(9):S57 (1998).
Sandborn et al., "An engineered human antibody to TNF (CDP571) for active Crohn's disease: a randomized double—blind placebo-controlled trial," Gastroenterology, 120:1330-1338 (2001).
Sandborn, "Antitumor necrosis factor for inflammatory bowel disease: A Review of agents, pharmacology, clinical results, and safety," Inflamm. Bowel Disease, 5(2):199-233 (1999).
Santora et al., "Characterization of Noncovalent Complexes of Recombinant Human Monoclonal Antibody and Antigen Using Carbon Exchange, Size Exclusion Chromatography,and BIAcore," Analytical Biochemistry, 299(2):119-129 (2001).

(56) References Cited

OTHER PUBLICATIONS

Santora et al., "Characterization of Recombinant Human Monoclonal Tissue Necrosis Factor-a Antibody Using Cation-Exchange HPLC and Capillary Isoelectric Focusing," Analytical Biochemistry, 275:98-108 (1999).
Schattenkirchner et al., "Long-term Use of the Fully Human Anti-TNF Antibody Adalimumab (D2E7) in Dmard-refractory Rheumatoid Arthritis," EULAR, Prague, Czech Republic, Jun. 2001.
Schattenkirchner et al., "Long-term Use of the Fully Human Anti-TNF Antibody D2E7 in Combination with Methotrexate in Active Rheumatoid Arthritis," EULAR 43(9) (suppl.) S228 (2000).
Schattenkirchner et al., "Phase 1 study on the effectiveness and compatibility of weekly subcutaneous injections of the human anti-TNF antibody D2E7 in chronic polyarthritis," Z. I Rheumatol., 58(1):1-42, p. 14 (1999).
Schiff et al., "A Randomized, Controlled, Safety Trial of Adalimumab (D2E7), a Fully Human Anti-TNF Monoclonal Antibody, Given to RA Patients in Combination with Standard Rheumatologic Care: The STAR (Safety Trial of Adalimumab in Rheumatoid Arthritis) Trial," Ann. Rheum .Dis., 61(1):S169 (2002).
Schiff et al., "Efficacy of Adalimumab Measured by the Disease Activity Score 28 (DAS28) and EULAR Response Criteria," Ann. Rheum. Dis., 62(1):170 (2003).
Schiff et al., "Malignancies in Rheumatoid Arthritis (RA) Clinical Trials with Adalimumab (Humira)," Arthritis Rheum., 48(9):S700 (2003).
Schiff et al., "Rates of Infection in Adalimumab Rheumatoid Arthritis Clinical Trials," Ann. Rheum. Dis., 62(1):184 (2003).
Schiff et al., "Sustained Efficacy of Adalimumab (HUMIRATM) Plus Methotrexate in Rheumatoid Arthritis (RA) Patients," Arthritis Rheum., 48(9):S314 (Poster 740) (2003).
Schmeling et al., "A combination of etanercept and methotrexate for the treatment of refractory juvenile idiopathic arthritis: a pilot study," Ann. Rheum. Dis., 60:410-412 (2001).
Shvidel et al., "Cytokine release by activated T-cells in large granular lymphocytic leukemia associated with autoimmune disorders," Hematol J., 3:32 (2002).
Sibilia, "Combination therapy for rheumatoid arthritis," Ann. Med. Interne., 153(1):41-52 (2002).
Siegel et al., "Evidence of Effects of a TNF Blocking Agent in ACR20 Non-Responders," Arthritis Rheum., 48(9):S127 (2003).
Skytta et al., "Etanercept and urticaria in patients with juvenile idiopathic arthritis," Clin. Exper. Rhematol., 18:533-534 (2000).
Smolen et al., "A Comparison of the SDAI and DAS28 as Measures of Response in Adalimumab (HUMIRAT) Clinical Trials in Rheumatoid Arthritis (RA)," Arthritis Rheum., 48(9):S107 (2003).
Smolen et al., "Objectives and Strategies for Rheumatoid Arthritis Therapy: Yesterday vs. Today," Drugs of Today, 39(B):3-8 (2003).
St. Clair et al., "Therapy of Rheumatoid Arthritis: New Developments and Trends," Curr. Rheumatol. Reports, 1(2):149-156 (1999).
Stone, et al., "Inadequate Calcium, Folic Acid, Vitamin E, Zinc and Selenium intake in Rheumatoid Arthritis Patients: results of a Dietary Survey," Semin Arthritis Rheum., 27(3):180-185 (1997).
Strand et al., "Improvement in Health-related Quality of Life, Health Utility, and Fatigue in Patients with Active Rheumatoid Arthritis (RA) on Adalimumab (Humira ™, Abbott) Therapy," Arthritis Rheum., 48(9):S402 (2003).
Strand et al., "Treatment with Adalimumab (D2E7), a Fully Human Anti-TNF Monoclonal Antibody, Improves Physical Function and Health Related Quality of Life (HRQOL) in Patients with Active Rheumatoid Arthritis (RA)," Ann. Rheum. Dis., 61(1):S175 (2002).
Strand. et al., "Adalimumab Improves Health-related Quality of Life in Rheumatoid Arthritis Patients," Ann. Rheum. Dis., 62(1):356 (2003).
Studnicka-Benke et al., "Tumor necrosis factor alpha and its soluble receptors parallel clinical disease and autoimmune activity in systemic lupus erythematosus," Br J Rheumatol., 35:1067 (1996).
Sun et al., "Bowel necrosis induced by tumor necrosis factor in rats is mediated by platelet-activating factor," J. Clin. Invest., 81:1328-1331 (1988).
Takei et al., "Safety and efficacy of high dose etanercept in treatment of juvenile rheumatoid arthritis," J. Rhematol., 28:1677-1680 (2001).
Takematsu, "Absence of tumor necrosis factor-alpha in suction blister fluids and stratum corneum from patients with psoriasis," Arch Dermatol Res., 281(6):398-400 (1989).
Taketani et al., "Comparison of cytokine levels and embryo toxicity in peritoneal fluid in infertile women with untreated or treated endometriosis," Am J Obstet. Gynecol., 167:265 (1992).
Taylor, "Anti-tumor necrosis factor therapies," Current Opinion in Rheumatology, 13:164-169 (2001).
The Lenercept Multiple Sclerosis Study Group and The University of British Columbia MS/MRI Analysis Group TNF neutralization in MS, "TNF neutralization in MS; Results of a randomized, placebo-controlled multicenter study," American Academy of Neurology, 53:457-465 (1999).
Thomas, Taber's Cyclopedic Medical Dictionary, 13:118-119 (1977).
Thomas, Taber's Cyclopedic Medical Dictionary, 17:1013-14 (1993).
Thompson et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," J. Mol. Biol., 256:77-88 (1996).
Thorp,"Tumour necrosis factor induction of ELAM-1 and ICAM-1 on human umbilical vein endothelial cells—analysis of tumour necrosis factor-receptor interactions," Cytokine, 4(4):313 (1992).
Tomlinson et al., "The Repertoire of Human Germline VH Sequences Reveals about Fifty Groups of VH Segments with Different Hypervariable Loops," J. Mol. Biol., 227:776-798 (1992).
Tomlinson et al., "The structural repertoire of the human VK domain," The EMBO Journal, 14(18):4628-4638 (1995).
Tracey et al., "Tumor Necrosis Factor: A Pleiotropic Cytokine and Therapeutic Target," Annu. Rev. Med., 45:491-503 (1994).
Tracy et al., "Shock and tissue injury induced by recombinant human cachectin," Science, 234:470-474 (1986).
Tripathi, M., "Drug Dosage," Essentials of Medical Pharmacology, 5(3):51-56 (2003).
Tsutsumimoto et al., "TNF-a and IL-1 B Suppress N-Cadherin Expression in MC3T3-E1 Cells," J Bone Miner Res., 14:1751 (1999).
Tugwell et al., "Adalimumab Improves Utility and Quality-adjusted Life Days in Rheumatoid Arthritis," Ann. Rheum. Dis., 62(1):107-8 (2003).
Tugwell et al., "Relationship Between ACR Response and HRQL in Adalimumab Clinical Trials," Ann. Rheum. Dis., 62(1):536 (2003).
Vajdos et al., "Comprehensive Functional Maps of the Antigen-binding Site of an Anti-ErbB2 Antibody Obtained with Shotgun Scanning Mutagenesis," J. Mol. Biol., 320:415-428 (2002).
Van Assche, "Anti-TNF agents in Crohn's Disease," Expert Opin. Investig. Drugs., 9(1):103-11 (2000).
Van de Putte et al., "Adalimumab (D2E7) Monotherapy in the Treatment of Patients with Severely Active Rheumatoid Arthritis (RA)," Arthritis Rheum., 46(9):S171 (2002).
Van de Putte et al., "A placebo-controlled phase 1 study of the human anti-TNP-antibody D2E7 in patients with active chronic polyarthritis," Z. Rheumatol., 58(1):1-34, F19 (1999).
Van de Putte et al., "A Single Dose Placebo Controlled Phase I Study of the Fully Human Anti-TNF Antibody D2E7 in Patients with Rheumatoid Arthritis," Arthritis Rheum., 41:S57 (1998).
Van De Putte et al., "Adalimumab (D2E7), the Fully Human Anti-TNF Monoclonal Antibody, in the Treatment of Patients with Rheumatoid Arthritis Who Failed Previous DMARD Therapy: Efficacy and Safety Results from a 6-Month Phase III Study," JCR, 8(3):S89 (2002).
Van de Putte et al., "Adaliumuab," TNFa-Inhibition in the Treatment of Rheumatoid Arthritis, 71-93 (2003).
Van de Putte et al., "Efficacy and Safety of Adalimumab (D2E7), the First Fully Human Anti-TNF Monoclonal Antibody, in Patients with Rheumatoid Arthritis Who Failed Previous DMARD Therapy: 6-Month Results from a Phase III Study," Ann. Rheum. Dis., 61(1):S168 (2002).

(56) References Cited

OTHER PUBLICATIONS

Van de Putte et al., "Efficacy and safety of adalimumab as monotherapy in patients with rheumatoid arthritis for whom previous disease modifying antirheumatic drug treatment has failed," Ann. Rheum Dis., 63:508-516 (2004).
Van de Putte et al., "Efficacy and safety of the fully human anti-tumour necrosis factor a monoclonal antibody adalimumab (D2E7) in DMARD refractory patients with rheumatoid arthritis: a 12 week, phase II study," Ann. Rheum. Dis., 62:1168-1177 (2003).
Van de Putte et al., "Efficacy of the Fully Human anti-TNF Antibody D2E7 in Rheumatoid Arthritis," Arthritis & Rheumatism, 42(1977):S400 (1999).
Van de Putte et al., "One Year Efficacy Results of the Fully Human Anti-TNF Antibody D2E7 in Rheumatoid Arthritis," Arthritis Rheum., 43(9):S269 (2000).
Van de Putte et al., "Sustained 5-Year Efficacy of Adalimumab (Humira) Monotherapy in DMARD-Refractory rheumatoid arthritis (RA)," Arthritis Rheum., 48(9):S314 (2003).
van der Heijdge et al. "Adalimumab improves health-related quality of life in patients with active ankylosing spondylitis—the ATLAS trial," Arthritis & Rheumatism, 52(9):Suppl. S., S211 (2005).
van der Poll et al., "Effect of postponed treatment with an anti-tumour necrosis factor (TNF) F(ab')2 fragment on endotoxin-induced cytokine and neutrophil responses in chimpanzees," Clin. Exp. Immunol., 100:21-25 (1995).
van Riel et al., "Long-Term Treatment with Adalimumab (D2E7) Using Background Methotrexate in Active Rheumatoid Arthritis: Results of a 3 Year Study," Arthritis Rheum., 46(9):S534 (2002).
Vasilli, "The pathophysiology of tumor necrosis factors", Annu. Rev. Immunol., 10:411-452 (1992).
Vaughan et al., "Human antibodies by design," Nature Biotechnology, 16:535-539 (1998).
Vazquez et al., "Adalimumab therapy for childhood uveitis," Journal of Pediatrics, 149(4): 572-575 (2006).
Velagapudi et al., "Pharmacokinetics of Adalimumab (D2E7), a Fully Human Anti-TNF-a Monoclonal Antibody, Following a Single Intravenous Injection in Rheumatoid Arthritis Patient Treated with Methotrexate," Arthritis Rheum., 46(9):S133 (2002).
Velagapudi, et al., "Effect of Methotrexate (MTX) Coadministration on the Pharmacokinetics (PK) of Adalimumab (Humira™, Abbott) Following a Single Intravenous (iv) Injection," Arthritis Rheum., 48(9):S141 (2003).
Venn et al., "Elevated synovial fluid levels of interleukin-6 and tumor necrosis factor associated with early experimental canine osteoarthritis," Arthritis Rheum., 36:819-826 (1993).
Vitali et al., "Preliminary criteria for the classification of Sjogren's syndrome," Arthritis Rheum, 36:3407 (1993).
Wailoo et al., "Modeling the cost effectiveness of etanercept, adalimumab and anakinra compared to infliximab in the treatment of patients with rheumatoid arthritis in the Medicare program," Agency for Healthcare Research and Quality, 1-74 (2006).
Wakefield et al., "The role of cytokines in the pathogenesis of inflammatory eye disease," Cytokine, 4:1 (1992).
Ward et al., "Binding activities of a repertoire of single immunoglobulin variable domains secreted from *Escherichia coli*," Nature, 341:544-546 (1989).
Weinblatt et al., "Adalimumab, a Fully Human Anti-Tumor Necrosis Factor a Monoclonal Antibody, for the Treatment of Rheumatoid Arthritis in Patients Taking Concomitant Methotrexate," Arthritis & Rheumatism, 48(1):35-45 (2003).
Weinblatt et al., "The ARMADA Trial: Efficacy and Safety of Adalimumab in Patients with Active RA at 24 Months," Ann. Rheum. Dis., 62(1):98 (2003).
Weinblatt et al., "The Armada Trial: Sustained Improvement and Tolerability in Long-Term Follow-Up of Patients Treated with Adalimumab (Humira™)," Arthritis Rheum., 48(9):S314 (2003).
Weisman et al., "A Dose Escalation Study Designed to Demonstrate the Safety, Tolerability and Efficacy of the Fully Human Anti-TNF Antibody, D2E7, Given in Combination with Methotrexate," Arthritis Rheum., 43(9):S391 (2000).
Weisman et al., "Efficacy, Pharmacokinetic, and Safety Assessment of Adalimumab, a Fully Human Anti-Tumor Necrosis Factor-Alpha Monoclonal Antibody, in Adults with Rheumatoid Arthritis Receiving Concomitant Methotrexate: A Pilot Study," Clinical Therapeutics, 25(6): 1700-1721 (2003).
Weisman et al., The Importance of Pain and the Impact of Adalimumab on Pain in RA Patients, Ann. Rheum. Dis., 62(1):351 (2003).
Weiss et al., "Juvenile idiopathic arthritis," Pediatric Clinics of North America, 52(2): 413-442 (2005).
Wellbome et al., "Adalimumab (D2E7), a Fully Human Anti-TNF-a Monoclonal Antibody, Improved Health-Related Quality of Life in Patients with Active Rheumatoid Arthritis Despite Concomitant Methotrexate Therapy," Arthritis Rheum., 46(9):S518 (2002).
Wells et al., "Incidence of Injection-Site Reactions Associated with Adalimumab (D2E7) Give Subcutaneously for at Least 6 Months: A Retrospective Analysis of 4 Phase II/III Clinical Trials," Arthritis Rheum., 46(9):S171 (2002).
Wells et al., "Injection-site Reactions in Adalimumab Rheumatoid Arthritis (RA) Pivotal Clinical Trials," Ann. Rheum. Dis., 62(1):411 (2003).
Wendling et al., "Anti-TNF-alpha therapy in ankylosing spondylitis," Expert Opinion on Pharmacotherapy, 5(7):1497-1507 (2004).
Westacott et al., "Tumor necrosis factor-a receptor expression on chondrocytes isolated from human articular cartilage," J. Rheumatology, 21:1710 (1994).
Williams et al., "Anti-tumor necrosis factor ameliorates joint disease in murine collagen-induced arthritis," Proc Natl Acad Sci USA, 89:9784 (1992).
Winter et al., "Humanized antibodies," Immunology Today, 14(6):243-246 (1993).
Winter et al., "Making Antibodies by Phage Display Technology," Annu. Rev. Immunol., 12:433-455 (1994).
Woon et al., "Kinetics of cytokine production in experimental autoimmune anterior uveitis (EAAU)," Current Eye Research, 17:955 (1998).
Yim Deong-Seok et al., "Population pharmacokinetic analysis and simulation of the time-concentration profile of etanercept in pediatric patients with juvenile rheumatoid arthritis", Journal of Clinical Pharmacology, vol. 45, No. 3, Mar. 1, 2005, pp. 246-256.
Barrios et al., "Length of the antibody heavy chain complementarity determining region 3 as a specificity-determining factor," J. Mol. Recognit, 17:332-338 (2004).
Brunner et al., "Preliminary definition of disease flare in juvenile rheumatoid arthritis," J. Rheum., 29:1058-1064 (2002).
Ching et al., "Induction of Intratumoral Tumor Necrosis Factor (TNF) Synthesis and Hemorrhagic Necrosis by 5,6-Dimethylxanthenone-4-Acetic Acid (DMXAA) in TNF Knockout Mice," Cancer Research, 59:3304-3307 (1999).
Clinical Trial NCT00048542, "A Multicenter, Randomized, Double-Blind, Placebo-Controlled Study of the Safety, Efficacy, and Pharmacokinetics of the Human Anti-TNF Monoclonal Antibody Adalimumab in Children With Polyarticular Juvenile Idiopathic Arthritis," WayBackMachine, (2002).
Clinical Trial NCT00048542, "Study of Human Anti-TNF Monoclonal Antibody Adalimumab in Children With Polyarticular Juvenile Idiopathic Arthritis (JIA)," Aug. 18, 2011 ClinicalTrials.gov Identifier: NCT00048542.
Colman, "Effects of amino acid sequence changes on antibody-antigen interactions," Research in Immunology, 145(1 ):33-36 (1994).
Dhillon et al., "Etanercept: A Review of its Use in the Management of Rheumatoid Arthritis," Drugs 67(8): 1211-1241(2007).
Garrison et al., "Etanercept: Therapeutic Use in patients With Rheumatoid Arthritis," Ann. Rheum. Dis. 58(Suppl. I):I65-I69 (1999).
Piatesi et al., "Immunological optimization of a generic hydrophobic pocket for high affinity hapten binding and diels-alder activity," ChemBioChem, 5:460-466 (2004).

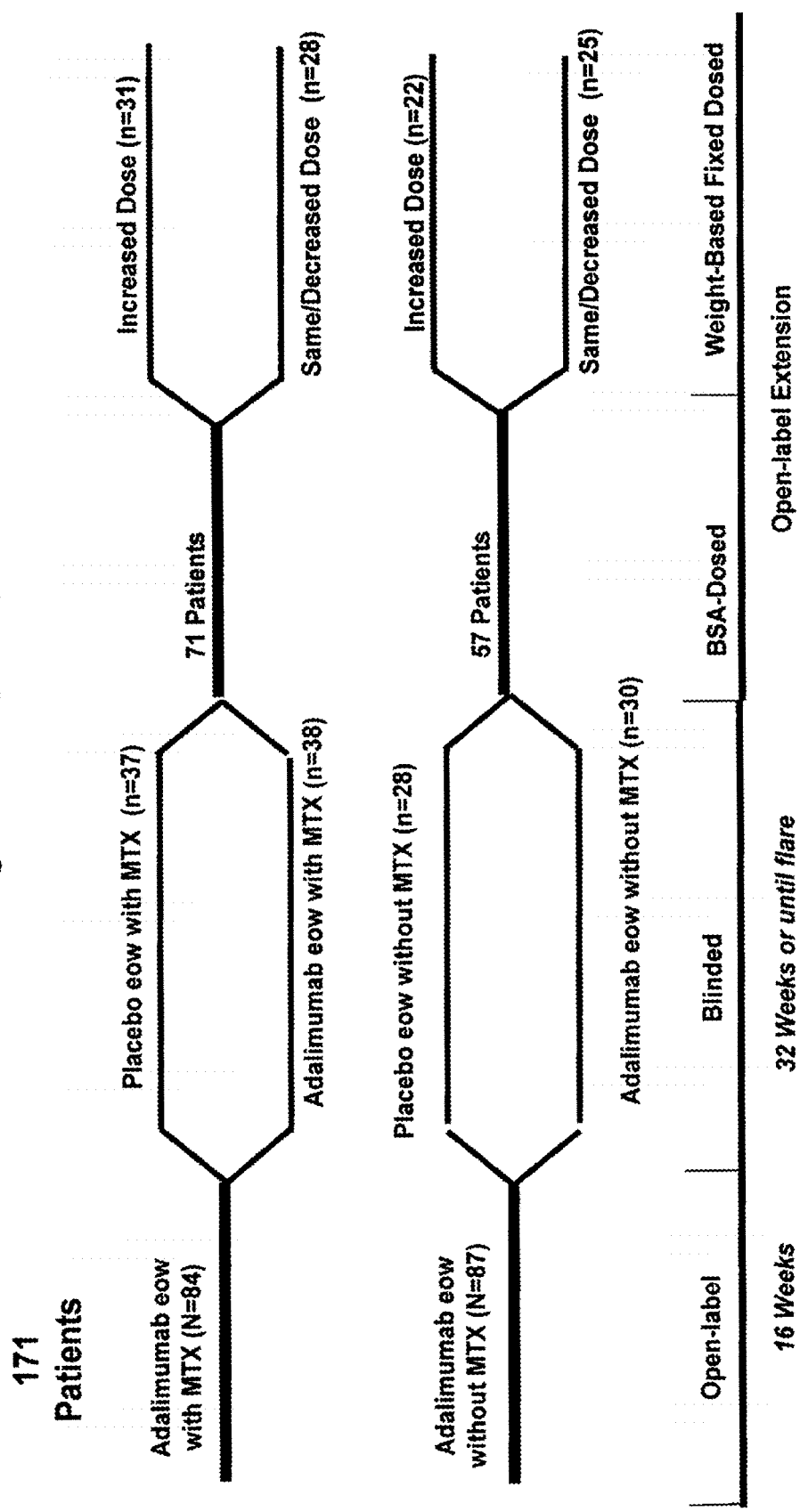
Figure 1. Study Design

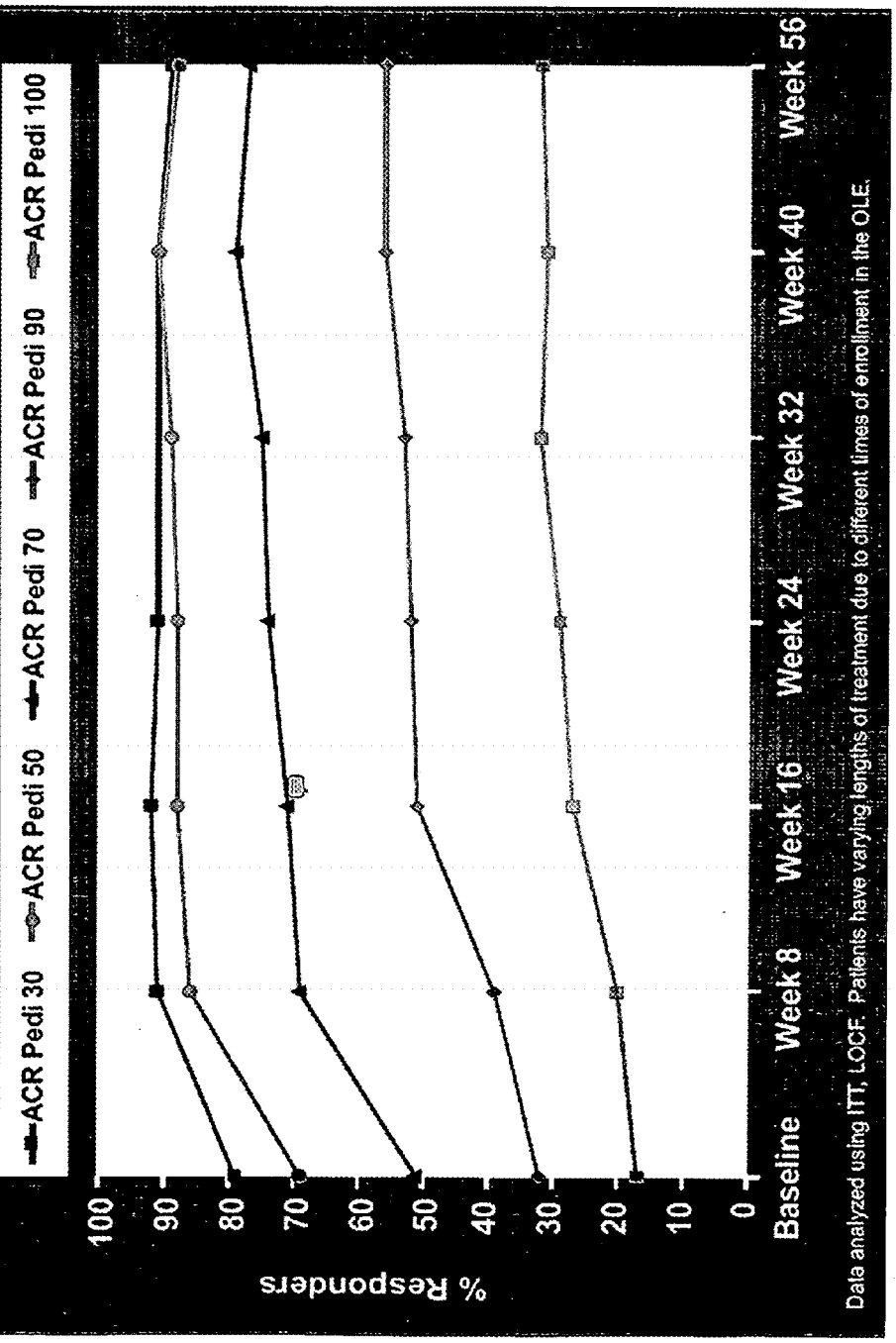

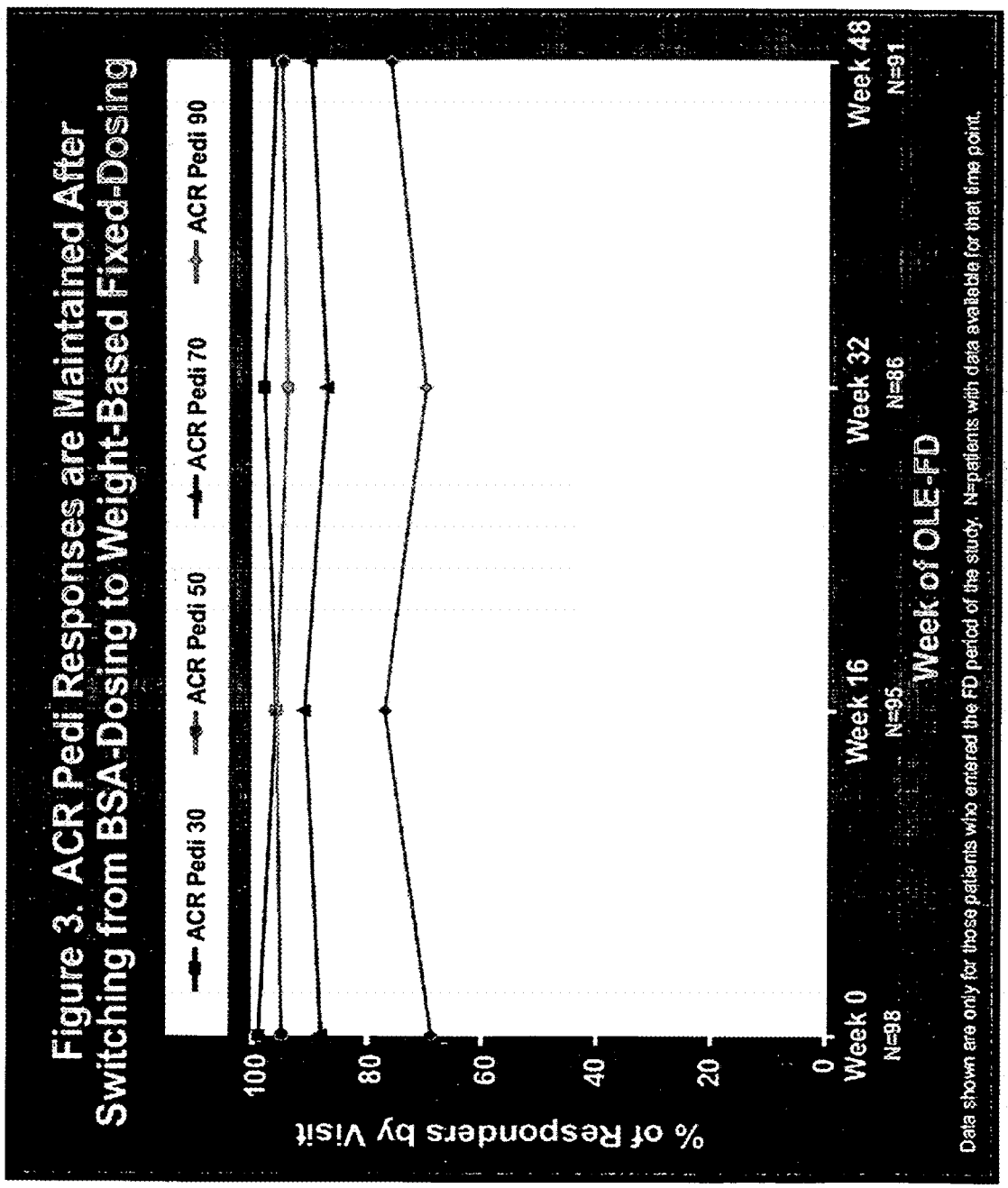

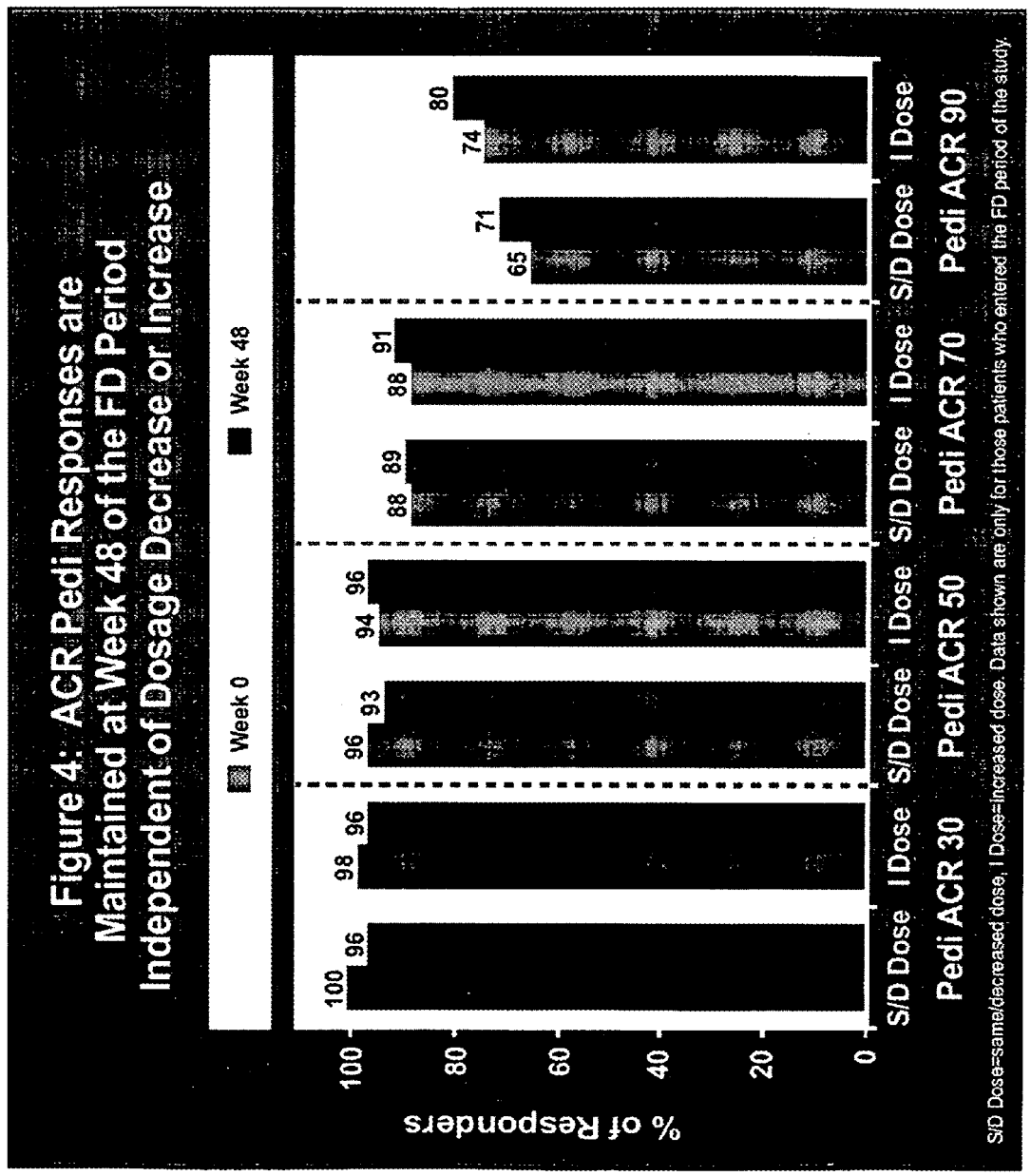

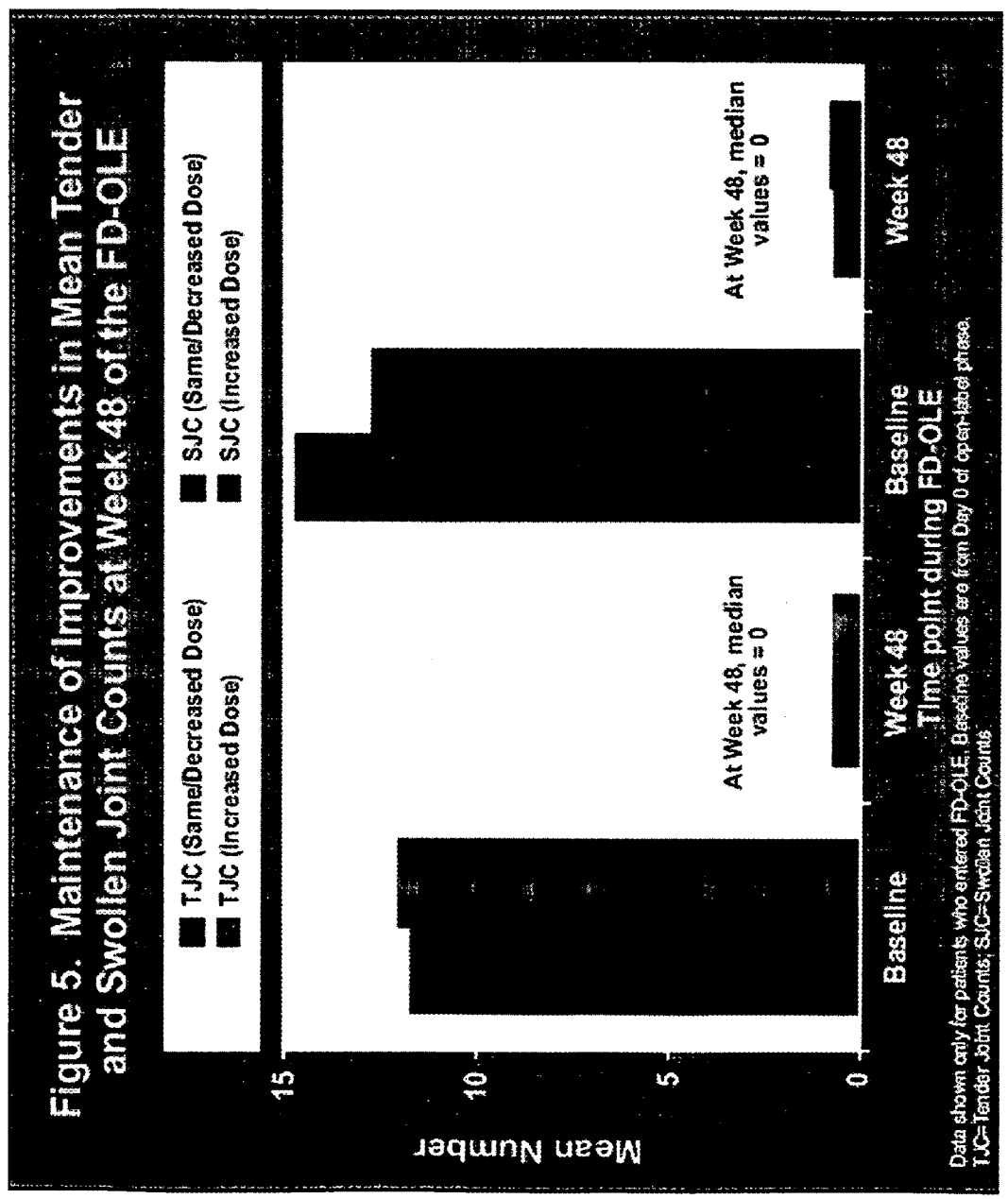
Figure 5. Maintenance of Improvements in Mean Tender and Swollen Joint Counts at Week 48 of the FD-OLE

SEQUENCE LISTING

<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105
```

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120
```

<210> SEQ ID NO 3
<211> LENGTH: 9

-continued

```
<212> TYPE: PRT
<213> ORGANISM: Artificial Sequence
<220> FEATURE:
<223> OTHER INFORMATION: adalimumab light chain variable region CDR3
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8
```

Asp Tyr Ala Met His
1               5

<210> SEQ ID NO 9
<211> LENGTH: 107
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Leu Ser Ala Ser Ile Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
    50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

```
Gln Lys Tyr Asn Ser Ala Pro Tyr Ala
 1               5

<210> SEQ ID NO 12
<211> LENGTH: 9
<212> TYPE: PRT
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
 1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
 1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
 1               5

<210> SEQ ID NO 17
<211> LENGTH: 9
<212> TYPE: PRT
<213> ORGANISM: Artificial Sequence
<220> FEATURE:
<223> OTHER INFORMATION: LOE5 light chain variable region CDR3

<400> SEQUENCE: 17

Gln Lys Tyr Asn Ser Ala Pro Tyr Tyr
```

```
<210> SEQ ID NO 18
<211> LENGTH: 9
<212> TYPE: PRT
<213> ORGANISM: Artificial Sequence
<220> FEATURE:
<223> OTHER INFORMATION: VLLOG7 light chain variable region CDR3

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial Sequence
<220> FEATURE:
<223> OTHER INFORMATION: VLLOG9 light chain variable region CDR3

<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: VLLOH1 light chain variable region CDR3

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial Sequence
<220> FEATURE:
<223> OTHER INFORMATION: VLLOH10 light chain variable region CDR3

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr
1               5

<210> SEQ ID NO 23
<211> LENGTH: 9
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
1               5
```

```
<210> SEQ ID NO 24
<211> LENGTH: 9
<212> TYPE: PRT
<213> ORGANISM: Artificial Sequence
<220> FEATURE:
<223> OTHER INFORMATION: VL0.1F4 light chain variable region CDR3

<400> SEQUENCE: 24

Gln Lys Tyr Ile Ser Ala Pro Tyr Thr
 1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
 1               5

<210> SEQ ID NO 26
<211> LENGTH: 9
<212> TYPE: PRT
<213> ORGANISM: Artificial Sequence
<220> FEATURE:
<223> OTHER INFORMATION: L0E7.A light chain variable region CDR3

<400> SEQUENCE: 26

Gln Arg Tyr Asn Arg Ala Pro Tyr Ala
 1               5

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
 1               5                  10
```

```
<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
 1               5                  10
```

```
<210> SEQ ID NO 36
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                               321

<210> SEQ ID NO 37
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tggagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                  363
```

US 9,284,370 B1

METHODS FOR TREATING JUVENILE IDIOPATHIC ARTHRITIS

RELATED APPLICATIONS

This application claims the benefit of priority to U.S. provisional patent application No. 60/934,310, filed on Jun. 11, 2007; U.S. provisional patent application No. 61/002,125, filed on Nov. 5, 2007; and U.S. provisional patent application No. 61/066,943, filed on Feb. 25, 2008. The contents of the above-mentioned priority applications are hereby incorporated by reference in its entirety

BACKGROUND

Juvenile idiopathic arthritis (JIA) (also known as juvenile rheumatoid arthritis (JRA), juvenile chronic polyarthritis, or Still's disease) is the most common rheumatic disease of childhood and an important cause of disability among children. JIA is an arthritis that causes joint inflammation and stiffness for more than 6 weeks in a child less than 16 years of age. In this disease, the immune system mistakenly targets the synovium. The synovium responds by making excess synovial fluid, which leads to swelling, pain and stiffness. The inflammation can then spread to the surrounding tissues, eventually damaging cartilage and bone. Other areas of the body, including the eyes, kidneys, lungs and heart, also may be affected by the inflammation.

Without treatment, JIA can interfere with a child's normal growth and development. Similar to the therapy of adult RA patients, disease-modifying antirheumatic drugs (DMARDs) and NSAIDs are often used to treat JIA. In recent years, tumor necrosis factor (TNF) has been identified as an important cytokine in the pathogenesis of JIA. Tumor necrosis factor has been implicated in the pathophysiology of juvenile arthritis, including juvenile idiopathic arthritis (Grom et al. (1996) *Arthritis Rheum.* 39:1703; Mangge et al. (1995) *Arthritis Rheum.* 8:211). Biologic response modifiers that inhibit TNF activity have become a new option for treatment of JIA, including infliximab, etanercept, and adalimumab (Ruperto et al. Clin Exp Rheumatol 2004; 22(4):522)).

Children present a unique challenge for dosing in general, as pediatric patient populations present a large range of weights and developmental ages. As such, treatment of JIA has often involved using a strict weight-based dosing scheme. For example, Ruperto et al. Arthritis Rheum. 2007 September; 56(9):2815-6 describes a combination therapy of infliximab and methotrexate for the treatment of JRA, where infliximab was administered at a dose of 3 mg/kg or 6 mg/kg. Similarly, etanercept may be used for the treatment of JIA and is delivered on a strict weight based dosing scheme, i.e., 0.8 mg/kg (see Enbrel® label; see also Lovell et al. Arthritis Rheum. 2003 January; 48(1):218-26).

For all patients, the goals of therapy are to decrease chronic joint pain and suppress the inflammatory process. Accomplishing these goals leads not only to improved short-term and long-term function but also to normal growth and development. JIA presents a unique challenge, not only for providing effective treatments but also for providing treatment regimens and agents which are appropriate for the young patient population associated with JIA.

SUMMARY OF THE INVENTION

Although TNFα inhibitors have been shown to be effective at treating juvenile idiopathic arthritis (JIA), there remains a need for improved treatment options for subjects suffering from JIA. The instant invention provides an improved means for treating a juvenile idiopathic arthritis (JIA) using a fixed dose of a TNFα inhibitor. The present invention provides a number of advantages over more traditional dosing regimens for JIA, i.e., strict weight-based dosing or mg/kg dosing schemes. Identifying a fixed dose which is effective for all patients in a given population, however, is a challenge, especially given the variability of a pediatric patient population.

The instant invention is based on the discovery that JIA may be treated using a TNFα inhibitor and a fixed dosing regimen. By providing a pre-determined amount of a TNFα inhibitor which is effective for treating JIA, the therapeutic agent may be administered more accurately, as weighing and measuring a dose amount no longer necessary. A fixed dose amount of a TNFα inhibitor results in better compliance and safer, more effective treatment.

The instant invention provides improved methods and compositions for treating JIA. Kits and labels which provide information pertaining to the methods, uses, and compositions of the invention are also described herein.

The invention includes a method for treating juvenile idiopathic arthritis (JIA) in a subject comprising administering a TNFα inhibitor to the subject, wherein the TNFα inhibitor is administered to the subject according to a fixed dosing regimen.

The invention also provides a method for treating juvenile idiopathic arthritis (JIA) in a subject comprising subcutaneously administering a human TNFα antibody, or antigen-binding portion thereof, to the subject, wherein the TNFα inhibitor is administered to the subject according to a fixed dosing regimen.

In one embodiment, the TNFα inhibitor is administered on a weight-based fixed dosing regimen. In one embodiment, the weight-based fixed dosing regimen comprises administering 20 mg of the TNFα inhibitor to the subject if the subject weighs less than 30 kg. In another embodiment, the weight-based fixed dosing regimen comprises administering 40 mg of the TNFα inhibitor to the subject if the subject weighs 30 kg or more.

The invention provides a method for treating juvenile idiopathic arthritis (JIA) in a subject comprising administering a TNFα inhibitor, such as a TNFα antibody, or antigen-binding portion thereof, wherein the TNFα inhibitor is administered to the subject at a fixed dose.

In one embodiment, the fixed dosing regimen is initiated when the subject achieves maintenance of a Ped ACR response, e.g., PedACR30, PedACR50, PEdACR70.

The invention also provides a method for maintaining an improved response, e.g., PedACR30, PedACR50, PedACR70, in a subject having juvenile idiopathic arthritis (JIA) comprising administering a fixed dose or a weight-based fixed dose of a TNFα inhibitor to the subject such that maintenance of the improved response is achieved.

The invention provides an article of manufacture comprising a packaging material; a TNFα inhibitor; and a label or package insert contained within the packaging material describing a method for administering a fixed dose of the TNFα, inhibitor for the treatment of JIA.

In one embodiment, the fixed dose is dependent on the subject's weight or is delivered as a weight-based fixed dose. In one embodiment, the invention provides a method for treating JIA comprising administering a weight-based fixed dose of adalimumab, e.g., over or equal to 30 kg requires a certain dose amount and under 30 kg requires a different dose amount.

In one embodiment, a dose of about 40 mg of adalimumab is administered if the subject is equal to or greater than 30 kg.

In one embodiment, a dose of about 20 mg of adalimumab is administered if the subject less than 30 kg.

In one embodiment, a given dose amount is administered to the subject if the subject is equal to or greater than 30 kg. In another embodiment, if the subject is less than 30 kg, then half of the dose amount determined for a subject who is equal to or greater than 30 kg is administered to the subject.

In addition, the invention provides a method for treating juvenile idiopathic arthritis (JIA) comprising first administering a TNFα inhibitor, such as a TNFα antibody, or antigen-binding portion thereof, to a subject on a body surface area (BSA) dosing regimen, and subsequently administering the TNFα, inhibitor according to a fixed dosing regimen. In one embodiment, the subject was administered a previous therapy comprising a body surface area (BSA) dosing regimen.

The invention provides a method for treating juvenile idiopathic arthritis (JIA) comprising first administering a TNFα inhibitor, such as a TNFα, antibody, or antigen-binding portion thereof, to a subject on a BSA dosing regimen, and subsequently administering the TNFα inhibitor according to a fixed dosing regimen, wherein about 40 mg of the TNFα, inhibitor is administered if the subject is equal to or over 30 kg, and about 20 mg of the TNFα inhibitor is administered if the subject is less than 30 kg in weight. In one embodiment, the fixed dosing regimen is initiated when the subject achieves maintenance of a Ped ACR response, e.g., PedACR30, PedACR50, PedACR70.

The invention also provides a method of improving a PedACR score, e.g., PedACR30, PedACR50, PedACR70, PedACR90, by administering a fixed dose of a TNFα inhibitor to a subject in need thereof. The invention further provides a method for improving the active joint count (AJC), improving the number of joints with limitation of passive limitation (LOM), improving a parent's or patient's assessment of pain (PaP), improving the disability index of the Children's Health Assessment Questionnaire (CHAQ DI), or improving the physician's global assessment of disease activity (PhDA) score by administering a TNFα inhibitor as a fixed dose to a subject having JIA.

The invention also includes a method of treating JIA achieving a mean steady-state trough serum TNFα inhibitor of 6.6 µg/mL and 8.1 µg/mL by administering the TNFα inhibitor as monotherapy or with concomitant methotrexate were, respectively. In one embodiment, said pharmacokinetic levels are achieved by administering 40 mg of adalimumab subcutaneously every other week in subjects weighing ≥30 kg.

The invention further provides a method for treating juvenile idiopathic arthritis (JIA) in a subject comprising administering a TNFα, inhibitor to the subject, wherein a mean steady-state trough serum of the TNFα inhibitor is about 6 to 7 µg/mL. In one embodiment, the TNFα inhibitor is administered to the subject as a monotherapy. In one embodiment, the subject weighs more than or equal to 30 kg. In another embodiment, the subject weighs less than 30 kg.

Also included in the invention is a method for treating juvenile idiopathic arthritis (JIA) in a subject comprising administering a TNFα inhibitor to the subject, wherein a mean steady-state trough serum of the TNFα inhibitor is about 8 to 9 µg/mL. In one embodiment, the TNFα, inhibitor is administered to the subject in combination with methotrexate. In one embodiment, the subject weighs more than or equal to 30 kg.

The invention further provides a method for treating juvenile idiopathic arthritis (JIA) in a subject comprising administering a TNFα inhibitor to the subject, wherein a mean steady-state trough serum of the TNFα inhibitor is about 10-11 µg/mL. In one embodiment, the TNFα inhibitor is administered to the subject in combination with methotrexate. In one embodiment, the subject weighs less than 30 kg.

The invention also provides a method of treating JIA achieving a mean steady-state trough serum TNFα inhibitor of about 6.8 µg/mL (6-7 µg/mL) and 10.9 µg/mL (10-11 µg/mL) by administering the TNFα inhibitor as monotherapy or with concomitant methotrexate were, respectively. In one embodiment, said pharmacokinetic levels are achieved by administering 20 mg of adalimumab subcutaneously every other week in subjects weighing <30 kg.

The invention also provides an article of manufacture comprising a TNFα inhibitor and a label or package insert, wherein the label or package insert indicates that the TNFα inhibitor may be used to treat JIA by administering a fixed dose amount to a subject in need thereof.

In one embodiment, the TNFα antibody, or antigen-binding portion thereof, is selected from the group consisting of adalimumab, infliximab, and golimumab.

In one embodiment, the TNFα inhibitor is administered weekly to a patient population. In one embodiment, the TNFα inhibitor is administered biweekly to a patient population.

In one embodiment, the TNFα inhibitor, e.g. antibody, is administered to the subject on a biweekly dosing regimen. In one embodiment, the TNFα inhibitor, e.g. antibody, is administered to the subject on weekly. In another embodiment, the TNFα inhibitor is administered to the subject on every other week. In one embodiment, the TNFα inhibitor is administered to the subject on once every four weeks. In one embodiment, the TNFα inhibitor is administered to the subject on once a month. In one embodiment, the TNFα inhibitor is administered to the subject on a dosing schedule which is not weekly.

In one embodiment, the TNFα inhibitor is administered as a monotherapy without an additional agent, such as methotrexate.

In another embodiment, the TNFα, inhibitor is administered with an additional therapeutic agent. In one embodiment, the TNFα inhibitor is administered with methotrexate. In one embodiment, the subject is administered methotrexate in combination with the TNFα inhibitor.

In one embodiment, the TNFα inhibitor is selected from the group consisting of a TNFα antibody, or an antigen-binding portion thereof, a TNF a fusion protein, a TNF a receptor fusion protein, or a recombinant TNF binding protein.

In one embodiment, the TNF receptor fusion protein is etanercept.

In one embodiment, the TNFα antibody, or antigen-binding portion thereof, is infliximab or golimumab.

In one embodiment, the TNFα antibody, or antigen-binding portion thereof, is selected from the group consisting of a chimeric antibody, a humanized antibody, and a multivalent antibody. In one embodiment, the TNFα antibody, or antigen-binding portion thereof, is a human antibody.

In one embodiment, the TNFα antibody, or antigen-binding portion thereof, is an isolated human antibody that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less.

In one embodiment, the TNFα antibody is an isolated human antibody, or antigen-binding portion thereof, that dissociates from human TNFα with a $K_{off}$ rate constant of $1\times10^{-3}$ s$^{-1}$ or less, as determined by surface plasmon resonance; has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9; and has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment, the TNFα, antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2

In one embodiment, the human TNFα antibody, or antigen-binding portion thereof, is adalimumab.

In one embodiment, the TNFα, antibody, or antigen-binding portion thereof, is administered subcutaneously.

In one embodiment, the fixed dose comprises 20-160 mg. In another embodiment the fixed dose comprises 20-80 mg. In yet another embodiment, the fixed dose comprises 20 mg. In yet another embodiment, the fixed dose comprises 40 mg. In yet another embodiment, the fixed dose comprises 45 mg of the TNFα inhibitor. In one embodiment, the fixed dose comprises 50 mg of the TNFα inhibitor. In yet another embodiment, the fixed dose comprises 90 mg of the TNFα inhibitor. In one embodiment, the fixed dose comprises 100 mg of the TNFα inhibitor.

In one embodiment, BSA dosing regimen for the TNFα antibody, or antigen-binding portion thereof, is a 24 mg Ada/ $M^2$ BSA dose.

BRIEF DESCRIPTION OF THE FIGURES

FIG. 1 depicts the study design of a Phase III study used to evaluate the long-term efficacy and safety of adalimumab in children with juvenile rheumatoid arthritis (JRA).

FIG. 2 graphically depicts sustained ACR Pedi responses during the BSA-Open-Label Extension period. N=number of patients who completed visit at time point. Due to differing times of enrollment into the BSA-OLE, some patients did not reach later time points in the BSA-OLE period before entering the FD-OLE.

FIG. 3 presents data illustrating that ACR Pedi responses are maintained after switching from BSA dosing to weight-based fixed-dosing. Data shown are only for those patients who entered the FD period of the study. N=patients with data available for that time point.

FIG. 4 graphically depicts ACR Pedi responses, and shows that said responses were maintained at week 48 of the FD period, independent of dosage increase or decrease.

FIG. 5 shows the maintenance of improvements in Mean Tender and Swollen Joint Counts at Week 16 of the FD-Open-Label Extension. Data shown only for patients who entered FD-OLE. Baseline values are from Day 0 of open-label phase.

DETAILED DESCRIPTION OF THE INVENTION

I. Definitions

The term "dose," as used herein, refers to an amount of TNFα inhibitor which is administered to a subject.

The term "dosing", as used herein, refers to the administration of a substance (e.g., an anti-TNFα, antibody) to achieve a therapeutic objective (e.g., treatment of juvenile idiopathic arthritis).

A "dosing regimen" describes a treatment schedule for a TNFα inhibitor, e.g., a treatment schedule over a prolonged period of time and/or throughout the course of treatment. In one embodiment, the dosing regimen of the invention comprises administering a first fixed dose of a TNFα inhibitor at week 0 followed by a second fixed dose of a TNFα inhibitor on a biweekly dosing regimen. In one embodiment, the dosing regimen comprises administering a fixed dose of a TNFα inhibitor monthly. In one embodiment, the dosing regimen comprises administering a fixed dose of a TNFα inhibitor once every four weeks. In one embodiment, the dosing regimen comprises administering a fixed dose of a TNFα inhibitor on a schedule that is not weekly.

The term "fixed dosing regimen" refers to a dosing regimen which relies on a fixed dose amount of an agent for the treatment of a disorder. In a preferred embodiment, the fixed dosing regimen includes administering a fixed dose amount of a TNFα inhibitor for the treatment of JIA. A fixed dose refers to a pre-determined amount of an agent, e.g., 20 mg, 21 mg, 22 mg, 23 mg, 24 mg, 25 mg, 40 mg, 45 mg, 50 mg, 80 mg, 90 mg, 100 mg, etc. In one embodiment, a fixed dosing regimen includes a dosing regimen where a TNFα inhibitor is administered to a subject as a fixed dose consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc., beginning at the initial dose.

In one embodiment, the fixed dose amount depends on a characteristic of the subject, e.g., age or weight of the subject. The term "weight-based fixed dosing regimen" refers to a dosing regimen which includes administration of a fixed dose amount of an agent for the treatment of a disorder, where the fixed amount depends upon the weight of the subject. A "weight-based fixed dosing regimen" does not include a mg/kg dosing regimen. In one embodiment, the fixed dose of a TNFα inhibitor for the treatment of JIA depends on whether the subject having JIA weighs less than a given weight, e.g., 30 kg, or whether the subject having JIA weighs greater than/equal to a given amount, e.g., 30 kg.

The terms "biweekly dosing regimen", "biweekly dosing", and "biweekly administration", as used herein, refer to the time course of administering a substance (e.g., an anti-TNFα antibody) to a subject to achieve a therapeutic objective, e.g, throughout the course of treatment. The biweekly dosing regimen is not intended to include a weekly dosing regimen. Preferably, the substance is administered every 9-19 days, more preferably, every 11-17 days, even more preferably, every 13-15 days, and most preferably, every 14 days. In one embodiment, the biweekly dosing regimen is initiated in a subject at week 0 of treatment on continued thereon. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing methods are also described in US 20030235585, incorporated by reference herein.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-TNFα antibody and another drug. The other drug(s) may be administered concomitant with, prior to, or following the administration of an anti-TNFα antibody, or an antigen-binding portion thereof.

The term "treatment," as used within the context of the present invention, is meant to include therapeutic treatment, as well as prophylactic or suppressive measures, for the treatment of juvenile idiopathic arthritis. For example, the term treatment may include administration of a TNFα inhibitor prior to or following the onset of juvenile idiopathic arthritis thereby preventing or removing signs of the disease or disorder. As another example, administration of a TNFα inhibitor after clinical manifestation of juvenile rheumatoid arthritis to combat the symptoms and/or complications and disorders associated with juvenile idiopathic arthritis comprises "treatment" of the disease. Further, administration of the agent after onset and after clinical symptoms and/or complications have developed where administration affects clinical parameters of the disease or disorder and perhaps amelioration of the disease, comprises "treatment" of the juvenile idiopathic arthritis.

The term "juvenile idiopathic arthritis" or "JIA" refers to arthritis, i.e., inflammation (cellular damage) of the synovium (the lining of joints), with onset before 16 years of age. JIA is a chronic, inflammatory disease which occurs before age 16 that may cause joint or connective tissue damage. The terms "juvenile idiopathic arthritis" and "JIA" are used interchangeably throughout with the term "juvenile rheumatoid arthritis" and "JRA" (see also Ringold et al. (2005) *JAMA* 294 (13): 1722)). JIA is also referred to as juvenile chronic polyarthritis and Still's disease.

Those "in need of treatment" include mammals, such as humans, already having juvenile idiopathic arthritis, including those in which the disease or disorder is to be prevented.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" includes agents which interfere with TNFα activity. The term also includes each of the anti-TNFα human antibodies and antibody portions described herein as well as those described in U.S. Pat. Nos. 6,090,382; 6,258,562; 6,509,015, each of which is incorporated by reference. In one embodiment, the TNFα inhibitor used in the invention is an anti-TNFα antibody, or a fragment thereof, including, for example, infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Schering-Plough and Centocor, see WO 02/12502; U.S. Pat. No. 7,250,165; US 20030049725; PCT/US01/24785; US 20040120952; US20050123541; US20050249735; US20070298040; US20070003548; US20060018907; US20060246073; US20070196373; and US20080025976, each of which is incorporated by reference herein), and adalimumab (Humira® (adalimumab)® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein. In another embodiment, the TNFα inhibitor is a TNFα receptor fusion protein, e.g., etanercept (Enbrel®, Amgen; described in WO 91/03553 and WO 09/406476, incorporated by reference herein). In another embodiment, the TNFα inhibitor is a recombinant TNF binding protein (r-TBP-I) (Serono).

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety. In a preferred embodiment, the antibody, or antigen binding fragment thereof, used in the invention is an anti-TNFα antibody or TNFα antibody (terms used interchangeably herein).

The term "antigen-binding portion" or "antigen-binding fragment" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Binding fragments include Fab, Fab', F(ab')$_2$, Fabc, Fv, single chains, and single-chain antibodies. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (or domain antibody) (Ward et al. (1989) *Nature* 341:544-546), which consists of a VH or a VL domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Chimeric antibodies" refers to antibodies wherein one portion of each of the amino acid sequences of heavy and light chains is homologous to corresponding sequences in antibodies derived from a particular species or belonging to a particular class, while the remaining segment of the chains is homologous to corresponding sequences from another species. In one embodiment, the invention features a chimeric antibody or antigen-binding fragment, in which the variable regions of both light and heavy chains mimics the variable regions of antibodies derived from one species of mammals, while the constant portions are homologous to the sequences in antibodies derived from another species. In a preferred embodiment of the invention, chimeric antibodies are made by grafting CDRs from a mouse antibody onto the framework regions of a human antibody.

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or immmunogenicity.

The term "multivalent antibody" refers to an antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" or "dual specific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060, Queen et al., *Proc. Natl. Acad. Sci. USA* 86:10029-10033 (1989), U.S. Pat. No. 5,530,101, U.S. Pat. No. 5,585,089, U.S. Pat. No. 5,693,761, U.S. Pat. No. 5,693,762, Selick et al., WO 90/07861, and Winter, U.S. Pat. No. 5,225,539.

An "isolated antibody", as used herein, is intended to refer to an antibody that is substantially free of other antibodies having different antigenic specificities (e.g., an isolated antibody that specifically binds hTNFα is substantially free of antibodies that specifically-bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jonsson et al. (1991) *Biotechniques* 11:620-627; Johnsson et al. (1995) *J. Mol. Recognit.* 8:125; and Johanson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

Various aspects of the invention are described in further detail herein.

II. TNF Inhibitors

The invention provides improved uses and compositions for treating juvenile idiopathic arthritis with a TNFα inhibitor, e.g., a human TNFα, antibody, or an antigen-binding portion thereof. Compositions and articles of manufacture, including kits, relating to the methods and uses for treating juvenile idiopathic arthritis are also contemplated as part of the invention.

A TNFα inhibitor which is used in the methods and compositions of the invention includes any agent which interferes with TNFα activity. In a preferred embodiment, the TNFα inhibitor can neutralize human TNFα, activity, particularly detrimental TNFα activity which is associated with juvenile idiopathic arthritis (HA).

In one embodiment, the TNFα inhibitor used in the invention is a TNFα antibody, or an antigen-binding fragment thereof, including chimeric, humanized, and human antibodies. Examples of TNFα, antibodies which may be used in the invention include, but not limited to, infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Schering-Plough and Centocor, described in WO 02/12502; U.S. Pat. No. 7,250,165; US 20030049725; PCT/US01/24785; US 20040120952; US20050123541; US20050249735; US20070298040; US20070003548; US20060018907; US20060246073; US20070196373; and US20080025976, each of which is incorporated by reference herein), and adalimumab (Humira® (adalimumab) Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein.

Other examples of TNFα inhibitors which may be used in the methods and compositions of the invention include etanercept (Enbrel, described in WO 91/03553 and WO 09/406476), soluble TNF receptor Type I, a pegylated soluble TNF receptor Type I (PEGs TNF-R1), p55TNFR1gG (Lenercept), and recombinant TNF binding protein (r-TBP-I) (Serono).

In one embodiment, the term "TNFα inhibitor" excludes infliximab. In one embodiment, the term "TNFα, inhibitor" excludes adalimumab. In another embodiment, the term "TNFα, inhibitor" excludes adalimumab and infliximab.

In one embodiment, the term "TNFα inhibitor" excludes etanercept, and, optionally, adalimumab, infliximab, or adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

In one embodiment, the invention features uses and composition of a TNFα, inhibitor for the treatment of juvenile idiopathic arthritis, wherein the TNFα inhibitor is a TNFα antibody, or antigen-binding portion thereof. In one embodiment, the TNFα antibody is an isolated human antibody, or antigen-binding portion thereof, that binds to human TNFα with high affinity and a low off rate, and also has a high neutralizing capacity. Preferably, the human antibodies used in the invention are recombinant, neutralizing human anti-hTNFα antibodies. The most preferred recombinant, neutralizing antibody of the invention is referred to herein as D2E7, also referred to as Humira® (adalimumab)® or adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/Humira® (adalimumab)®) have been described in Salfeld et al., U.S. Pat. Nos. 6,090,382, 6,258,562, and 6,509,015, which are each incorporated by reference herein. The methods of the invention may also be performed using chimeric and humanized murine anti-hTNFα antibodies which have undergone clinical testing for treatment of idiopathic arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

In one embodiment, the method of the invention includes treatment of JIA using a fixed dose of a D2E7 antibody and antibody portion thereof, D2E7-related antibodies and antibody portions, or other human antibodies and antibody portions with equivalent properties to D2E7, such as high affinity binding to hTNFα with low dissociation kinetics and high neutralizing capacity, for the treatment of juvenile idiopathic arthritis. In one embodiment, the invention provides treatment with an isolated human antibody, or an antigen-binding portion thereof, that dissociates from human TNFα with a $K_d$ of $1 \times 10^{-8}$ M or less and a $K_{off}$ rate constant of $1 \times 10^{-3}$ or less, both determined by surface plasmon resonance, and neutralizes human TNFα cytotoxicity in a standard in vitro L929 assay with an $IC_{50}$ of $1 \times 10^{-7}$ M or less. More preferably, the isolated human antibody, or antigen-binding portion thereof, dissociates from human TNFα with a $K_{off}$ of $5 \times 10^{-4}$ s$^{-1}$ or less, or even more preferably, with a $K_{off}$ of $1 \times 10^{-4}$ s$^{-1}$ or less. More preferably, the isolated human antibody, or antigen-binding portion thereof, neutralizes human TNFα cytotoxicity in a standard in vitro L929 assay with an $IC_{50}$ of $1 \times 10^{-8}$ M or less, even more preferably with an $IC_{50}$ of $1 \times 10^{-9}$ M or less and still more preferably with an $IC_{50}$ of $1 \times 10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to treating juvenile idiopathic arthritis by administering human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382, incorporated by reference herein).

Accordingly, in another embodiment, the antibody or antigen-binding portion thereof preferably contains the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5 \times 10^{-4}$ s$^{-1}$ or less. Even more preferably, the antibody, or antigen-binding portion thereof, dissociates from human TNFα with a $K_{off}$ of $1 \times 10^{-4}$ s$^{-1}$ or less.

In yet another embodiment, the antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_\kappa$I human germline family, more preferably from the A20 human germline Vk gene and most preferably from the D2E7 VL framework sequences shown in FIGS. 1A and 1B of U.S. Pat. No. 6,090,382. The framework regions for VH preferably are from the $V_H3$ human germline family, more preferably from the DP-31 human germline VH gene and most preferably from the D2E7 VH framework sequences shown in FIGS. 2A and 2B of U.S. Pat. No. 6,090,382, incorporated by reference herein.

Accordingly, in another embodiment, the antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention includes uses of an isolated human antibody, or an antigen-binding portions thereof, containing D2E7-related VL and VH CDR3 domains. For example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the methods and compositions of the invention may be modified for improved treatment of juvenile idiopathic arthritis. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (Cl-ClO) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat juvenile idiopathic arthritis by administration of the TNFα, antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion used in the methods and compositions of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, used in the methods and compositions of the invention, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express adalimumab (D2E7) or an adalimumab (D2E7)-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Moreover, it should be noted that if the "germline" sequences obtained by PCR amplification encode amino acid differences in the framework regions from the true germline configuration (i.e., differences in the amplified sequence as compared to the true germline sequence, for example as a result of somatic mutation), it may be desirable to change these amino acid differences back to the true germline sequences (i.e., "backmutation" of framework residues to the germline configuration).

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of the foregoing, nucleic acid, vector and host cell compositions that can be used for recombinant expression of the antibodies and antibody portions used in the invention include nucleic acids, and vectors comprising said nucleic acids, comprising the human TNFα antibody adalimumab (D2E7). The nucleotide sequence encoding the D2E7 light chain variable region is shown in SEQ ID NO: 36. The CDR1 domain of the LCVR encompasses nucleotides 70-102, the CDR2 domain encompasses nucleotides 148-168 and the CDR3 domain encompasses nucleotides 265-291. The nucleotide sequence encoding the D2E7 heavy chain variable region is shown in SEQ ID NO: 37. The CDR1 domain of the HCVR encompasses nucleotides 91-105, the CDR2 domain encompasses nucleotides 148-198 and the CDR3 domain encompasses nucleotides 295-330. It will be appreciated by the skilled artisan that nucleotide sequences encoding D2E7-related antibodies, or portions thereof (e.g., a CDR domain, such as a CDR3 domain), can be derived from the nucleotide sequences encoding the D2E7 LCVR and HCVR using the genetic code and standard molecular biology techniques.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene Sur-fZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-65; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human neutralizing antibodies with high affinity and a low off rate constant for hTNFα are described in U.S. Pat. Nos. 6,090,382, 6,258,562, and 6,509,015, each of which is incorporated by reference herein.

Antibodies, antibody-portions, and other TNFα inhibitors for use in the methods of the invention, can be incorporated into pharmaceutical compositions suitable for administration to a subject. Typically, the pharmaceutical composition comprises an antibody, antibody portion, or other TNFα, inhibitor, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor. Additional aspects relating to the administration of and pharmaceutical compositions comprising TNFα inhibitors for treating JIA on a fixed dose regimen are provided in Section III below.

III. Uses and Compositions for Treating Juvenile Idiopathic Arthritis (JIA)

The invention provides methods for treating JIA using a fixed dose regimen including administration of a TNFα inhibitor, e.g., a TNFα antibody, or antigen-binding portion thereof.

JIA causes joint inflammation and stiffness for more than 6 weeks in a child of 16 years of age or less. Inflammation causes redness, swelling, warmth, and soreness in the joints. Any joint can be affected and inflammation may limit the mobility of affected joints. One type of JIA can also affect the internal organs.

JIA is often classified into three types by the number of joints involved, the symptoms, and the presence or absence of certain antibodies found by a blood test. These classifications help the physician determine how the disease will progress and whether the internal organs or skin is affected. The classifications of JIA include the following a. Pauciarticular JIA, wherein the patient has four or fewer joints are affected. Pauciarticular is the most common form of JIA, and typically affects large joints, such as the knees.

b. Polyarticular JIA, wherein five or more joints are affected. The small joints, such as those in the hands and feet, are most commonly involved, but the disease may also affect large joints.

c. Systemic JIA is characterized by joint swelling, fever, a light skin rash, and may also affect internal organs such as the heart, liver, spleen, and lymph nodes. Systemic JIA is also referred to as it Still's disease. A small percentage of these children develop arthritis in many joints and can have severe arthritis that continues into adulthood.

The invention provides an improved means for treating a JIA using a fixed dose, i.e., a pre-determined given amount, of a TNFα inhibitor. A fixed dose stands in contrast to a mg/kg weight based dosing scheme, where the amount given to a subject is calculated according to the subject's weight. A fixed dose amount of a TNFα inhibitor simplifies the medication regimen, which in turn decreases the risk of medication non-compliance and translates into more effective treatment.

While strict weight based dosing, i.e., mg per kilogram (mg/kg) dosing, may be an effective means for determining the dose amount, a fixed dosing regimen provides a number of advantages. By using a fixed dose, the administration of the TNFα inhibitor is simplified and compliance is likely improved. Fixed doses also have improved safety considerations. For example, as therapeutic agents are generally provided in discrete amounts, dosing based on a specific characteristic of a subject, e.g., mg/kg or BSA, results in the subject administering what is needed, and often having to preserve the remainder of the therapeutic agent for future administration. In the case of biologics, such as the TNFα inhibitors adalimumab, etanercept, golimumab, and infliximab, storage of partially used vials of the agent may present safety concerns if such storage is not proper. Additionally, once a vial (or syringe, pen, etc) is opened for administration, sterility for future use cannot be assured. By using a fixed dose amount for the treatment of JIA, aforementioned safety issues may be avoided as the vial (or syringe, pen, etc.) contains the specific fixed dose. Upon delivery, the use of the vial is completed and the container properly disposed.

In one embodiment, the fixed dose amount of TNFα inhibitor ranges from 10-200 mg. In one embodiment, the fixed dose amount comprises a dose ranging from 20-160 mg of the TNFα inhibitor; 20-100 mg of the TNFα inhibitor; 20-90 mg of the TNFα inhibitor; 20-80 mg of the TNFα inhibitor; 20-70 mg of the TNFα inhibitor; 20-60 mg of the TNFα inhibitor; 20-50 mg of the TNFα inhibitor; or 20-40 mg of the TNFα inhibitor. Numbers intermediate to the above recited fixed dose amounts, e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc., as well as all other numbers recited herein, are also intended to be part of this invention. Ranges of values using a combination of any of the above recited values as upper and/or lower limits are intended to be included in the scope of the invention, e.g., 15-45, 20-25, 25-45, etc.

In one embodiment, the fixed dose amount of TNFα inhibitor comprises a fixed dose amount of 20 mg, 40 mg, 45 mg, 50 mg, 90 mg, or 100 mg.

The fixed dosing regimen of the invention includes, in one embodiment, administering the fixed dose amount of the TNFα inhibitor according to a dosing schedule. In one embodiment, the fixed dose amount is administered to the subject for the treatment of JIA according to a biweekly dosing regimen. In another embodiment, the fixed dose amount is administered to the subject monthly for the treatment of JIA. Alternatively, the fixed dose amount is administered to the subject once every four weeks for the treatment of JIA. The fixed dose amount of the TNFα inhibitor may be administered as the initial dose of treatment in the dosing schedule.

The fixed dose amount of the TNFα inhibitor may be administered in accordance with whether the subject is above or below a given characteristic of the subject, such as, but not limited to, age or weight. Thus, in one embodiment, the fixed dosing regimen for treatment of juvenile idiopathic arthritis (JIA) is a weight-based fixed dose. A fixed dosing regimen which depends on the weight of a subject is referred to herein as a weight-based fixed dosing regimen, and is not equivalent to a strict weight based dosing regimen (mg/kg). For example, different fixed dose amounts may be administered to a subject having JIA depending on whether the subject weighs less than, equal to, or greater than 30 kg. It should be noted that 30 kg is provided as an exemplary weight and should not be used to limit the invention. Alternative weights for determining which fixed dose amounts include, but are not limited to, 25 kg, 26 kg, 27 kg, 28 kg, 29 kg, 30 kg, 31 kg, 32 kg, 33 kg, 34 kg, and 35 kg. In one embodiment, a weight based fixed dosing regimen comprises administering 20 mg of the TNFα inhibitor to the subject if the subject weighs less than 30 kg. In another embodiment, a weight based fixed dosing regimen comprises administering 40 mg of the TNFα inhibitor to the subject if the subject weighs 30 kg or more.

In one embodiment, the fixed dosing regimen includes different fixed dose amounts. For example, in instances where a given fixed dose is administered according the weight of the subject, e.g., 30 kg or less, a fixed dosing regimen would include changing the fixed dose should the subject at some point during treatment exceed the determined weight limitation for the different fixed doses. For example, a fixed dosing regimen includes administering 20 mg of a human TNFα antibody when the subject weighs less than 30 kg, and subsequently administering 40 mg of the human TNFα antibody when the subject weighs more than 30 kg.

In one embodiment, the invention provides a method for treating JIA comprising administering a TNFα inhibitor, e.g., a TNFα antibody, or antigen-binding portion thereof, on a fixed dosing regimen or in a combination dosing regimen, e.g., a fixed dosing regimen in combination with a BSA dosing regimen. A fixed dosing regimen may be used as the dosing regimen for the treatment of JIA with a TNFα inhibitor, where, for example, the subject is initially started on treatment based on a fixed dose and continues thereon. Alternatively, the fixed dosing regimen may be combined with a dosing regimen based on a specific characteristic of the subject, e.g., body surface area (BSA). In one embodiment, the TNFα antibody, or antigen-binding portion thereof, the BSA dosing regimen comprises administering a dose of about 20-30 mg according to the given body surface area of the subject, e.g., 24 mg/M$^2$ BSA. In one embodiment, the human TNFα antibody, or an antigen-binding portion thereof, is administered on a fixed dosing regimen in combination with a BSA-dosing regimen, wherein the BSA dose comprises about 24 mg adalimumab/M$^2$ BSA.

In one embodiment, the TNFα antibody, or antigen-binding portion thereof, is administered subcutaneously to the subject.

A dosage unit form or a fixed dose amount, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Dosage regimens described herein may be adjusted to provide the optimum desired response, e.g., maintaining remission of juvenile idiopathic arthritis, preventing flare-ups, in consideration of the teachings herein. It is to be noted that dosage values may vary with the type and severity of juvenile idiopathic arthritis (JIA). It is to be further understood that for any particular subject, specific dosage regimens may be adjusted over time according to the teachings of the specification in view of the individual need and the professional judgment of the person administering or supervising the administration of the compositions. It should further be understood that dosage amounts and ranges set forth herein are exemplary only and are not intended to limit the scope or practice of the claimed invention.

The compositions for use in the methods and compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In a preferred embodiment, the antibody or other TNFα inhibitor is administered by intravenous infusion or injection. In another preferred embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, the invention includes pharmaceutical compositions comprising a TNFα inhibitor and a pharmaceutically acceptable carrier, for treating juvenile idiopathic arthritis on a fixed dose regimen.

In one embodiment, the antibody or antibody portion for use in the methods of the invention is incorporated into a pharmaceutical formulation as described in PCT/IB03/04502 and U.S. Appln. No. 20040033228, incorporated by reference herein. This formulation includes a concentration 50 mg/ml of the antibody D2E7 (adalimumab), wherein one pre-filled syringe contains 20 or 40 mg of antibody for subcutaneous injection. Alternatively, a pen may be used to deliver 20 or 40 mg of antibody for subcutaneous injection.

The antibodies, antibody-portions, and other TNFα inhibitors of the present invention can be administered by a variety of methods known in the art, although for many therapeutic applications, the preferred route/mode of administration is parenteral, e.g., subcutaneous injection. In another embodiment, administration is via intravenous injection or infusion.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Dekker, Inc., New York, 1978.

In one embodiment, the TNFα antibodies and inhibitors used in the invention are delivered to a subject subcutaneously. In one embodiment, the subject administers the TNFα inhibitor, including, but not limited to, TNFα antibody, or antigen-binding portion thereof, to himself/herself. The TNFα inhibitor may be administered subcutaneously using a pre-filed syringe or, alternatively, a pen, such as an autoinjector pen described in PCT publication WO 2008/005315, incorporated in its entirety by reference herein.

The TNFα antibodies and inhibitors used in the invention may also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. Appln. No. 20040033228, incorporated by reference herein, are used to treat idiopathic arthritis using the treatment methods of the invention.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result, i.e., treatment of JIA. In consideration of the teachings herein, a therapeutically effective amount of the antibody, antibody portion, or other TNFα inhibitor may vary within the scope of the invention according to factors such as the disease state, age, sex, and weight of the individual, and the ability of the antibody, antibody portion, other TNFα, inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion for use in the methods of the invention is coformulated with and/or coadministered with one or more additional therapeutic agents, including an juvenile idiopathic arthritis inhibitor or antagonist. For example, an anti-hTNFα antibody or antibody portion of the invention may be coformulated and/or coadministered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

The TNFα inhibitor, e.g., TNFα antibody, or an antigen-binding portion thereof, may be administered to the subject on a biweekly, fixed dosing regimen in accordance with the teachings herein. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. In one embodiment, the methods of the invention comprising administering a TNFα, antibody, or an antigen-binding portion thereof, on a biweekly dosing regimen subcutaneously. Biweekly dosing regimens can be used to treat disorders in which TNFα activity is detrimental, and are further described in U.S. application Ser. No. 10/163,657 (US 20030235585), incorporated by reference herein. In one embodiment, a fixed dose amount of the TNFα inhibitor, e.g., TNFα antibody, or an antigen-binding portion thereof, is administered to the subject monthly.

In one embodiment, the invention provides a method of treating JIA in a subject comprising administering adalimumab, to the subject at week 0 on a biweekly, fixed dosing regimen. In one embodiment, the human TNFα, antibody, or antigen-binding portion thereof, is administered subcutaneously. In one embodiment, JIA is treated by administering adalimumab on biweekly dosing regimen for at least about 4 weeks, 5 weeks, 6 weeks, 7 weeks, 8 weeks, 9 weeks, 10 weeks, 11 weeks, 12 weeks, 13 weeks, 14 weeks, 15 weeks, for 16 weeks, for 17 weeks, for 18 weeks, for 19 weeks, for 20 weeks, for 21 weeks, for 22 weeks, for 23 weeks, for 24 weeks, for 25 weeks, for 26 weeks, for 27 weeks, for 28 weeks, for 29 weeks, for 30 weeks, for 31 weeks, for 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, or at least about 48 weeks.

Methods of treatment described herein may include administration of a TNFα inhibitor to a subject to achieve a therapeutic goal, e.g., improvement in PedACR response, improvement swollen joint count (SJC), increase in time until flare-up, and improvement in tender joint count (TJC). Also included in the scope of the invention are uses of a TNFα inhibitor in the manufacture of a medicament to achieve a therapeutic goal, e.g., improvement in PedACR response, swollen joint count (SJC), time until flare-up, and tender joint count (TJC). Thus, where methods are described herein, it is also intended to be part of this invention that the use of the TNFα inhibitor in the manufacture of a medicament for the purpose of the method is also considered within the scope of the invention. Likewise, where a use of a TNFα inhibitor in the manufacture of a medicament for the purpose of achieving a therapeutic goal is described, methods of treatment resulting in the therapeutic goal are also intended to be part of the invention.

Using the methods of the invention, JIA may be improved in subjects in need thereof using a index known in the art for determining patient improvements. Examples of such indices include, but are not limited to, a PedACR score, e.g., PedACR30, PedACR50, PedACR70, PedACR90, active joint count (AJC), number of joints with limitation of passive limitation (LOM), a parent's or patient's assessment of pain (PaP), the disability index of the Children's Health Assessment Questionnaire (CHAQ DI), or the physician's global assessment of disease activity (PhDA) score. Thus, the method of the invention may be used to improve such scores in a subject having JIA.

The Pediatric (Ped) ACR is a standardized set of definitions for remission and clinical improvement developed by the American College of Rheumatology (ACR) for measuring disease outcome and severity in patients with juvenile rheumatoid arthritis (see, for example, Giannini, et al. (1997) *Arthritis Rheum.* 40(7):1202-9). Improvement is denoted as either Ped ACR 20, ACR 50, ACR 70, or ACR 90 reflecting either an improvement from baseline in at least 3 of any 6 variables in the core set to the 20%, 50%, 70%, or 90% level, with no more than 1 of the remaining variables worsening by >30%. The variables in the core set consist of physician global assessment of disease activity, parent/patient assessment of overall well-being (each scored on a 10-cm Visual Analog Scale), functional ability, number of joints with active arthritis, number of joints with limited range of motion, and erythrocyte sedimentation rate. For example, an ACR20 response means clinical improvement indicated by a 20% improvement in the number of tender and swollen joints and a 20% improvement in at least three of five additional criteria. Other examples of indices which may be used for determining improvement in a subject having JIA are described in US Patent Application Publication No. 20080118496, incorporated by reference herein.

Articles of Manufacture

The invention also pertains to packaged pharmaceutical compositions or kits for administering a TNFα inhibitor using a fixed dosing regimen for the treatment of juvenile idiopathic arthritis. In one embodiment of the invention, the kit comprises a TNFα inhibitor, such as an antibody, and instructions for administration of the TNFα inhibitor for treatment of juvenile idiopathic arthritis. The instructions may describe how, e.g., subcutaneously, and when, e.g., at week 0, week 2, week 4, etc., the fixed doses of TNFα inhibitor shall be administered to a subject for treatment. The instructions may also include different fixed dose amounts that should be administered depending on the subject's weight.

The term "package insert" is used to refer to instructions customarily included in commercial packages of therapeutic products, that contain information about the indications, usage, dosage, administration, contraindications and/or warnings concerning the use of such therapeutic products.

Another aspect of the invention pertains to kits containing a pharmaceutical composition comprising a TNFα inhibitor, such as an antibody, and a pharmaceutically acceptable carrier and one or more pharmaceutical compositions each comprising an additional therapeutic agent useful for treating juvenile idiopathic arthritis, and a pharmaceutically acceptable carrier. Alternatively, the kit comprises a single pharmaceutical composition comprising an anti-TNFα antibody, one or more drugs useful for treating juvenile idiopathic arthritis, and a pharmaceutically acceptable carrier. The instructions may describe how, e.g., subcutaneously, and when, e.g., at week 0, week 2, week 4, etc., the fixed doses of TNFα inhibitor and/or the additional therapeutic agent shall be administered to a subject for treatment.

The kit may contain instructions for dosing of the pharmaceutical compositions for the treatment of juvenile idiopathic arthritis. Additional description regarding articles of manufacture of the invention are described in subsection III. The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

The invention also provides a packaged pharmaceutical composition wherein the TNFα inhibitor, e.g., TNFα antibody, is packaged within a kit or an article of manufacture. The kit or article of manufacture of the invention contains materials useful for the treatment, including how to administer a fixed dosing regimen to a subject, of juvenile idiopathic arthritis. The kit or article of manufacture comprises a container and a label or package insert or printed material on or associated with the container which provides information regarding use of the TNFα inhibitor, e.g., a TNFα antibody, for the treatment of juvenile idiopathic arthritis.

A kit or an article of manufacture refers to a packaged product comprising components with which to administer a TNFα, inhibitor for treatment of a juvenile idiopathic arthritis. The kit preferably comprises a box or container that holds the components of the kit. The box or container is affixed with a label or a Food and Drug Administration approved label, including a protocol for administering the TNFα inhibitor. The box or container holds components of the invention which are preferably contained within plastic, polyethylene, polypropylene, ethylene, or propylene vessels. The vessels can be capped-tubes or bottles. The kit can also include instructions for administering the TNFα antibody in accordance with the fixed dose of the invention. In one embodiment the kit of the invention includes the formulation comprising the human antibody adalimumab (or D2E7), as described in PCT/IB03/04502 and U.S. application Ser. No. 10/222,140, incorporated by reference herein.

In one embodiment, the article of manufacture of the invention comprises (a) a first container with a composition contained therein, wherein the composition comprises a TNFα antibody; and (b) a package insert indicating that the TNFα antibody may be used for reducing signs and symptoms and inducing and maintaining remission of juvenile idiopathic arthritis. In a preferred embodiment, the label or package insert indicates that the TNFα inhibitor, e.g., a TNFα antibody, is used for inducing and maintaining remission juvenile idiopathic arthritis.

Suitable containers for the TNFα inhibitor, e.g., a TNFα antibody, include, for example, bottles, vials, syringes, pens, etc. The containers may be formed from a variety of materials such as glass or plastic. The container holds a composition which is by itself or when combined with another composition effective for treating, preventing and/or diagnosing the condition and may have a sterile access port.

In one embodiment, the article of manufacture comprises a TNFα inhibitor, e.g., a TNFα antibody, and a label which indicates to a subject who will be administering the TNFα inhibitor about using the TNFα inhibitor for the treatment of juvenile idiopathic arthritis, including polyarticular JIA. The label may be anywhere within or on the article of manufacture. In one embodiment, the article of manufacture comprises a container, such as a box, which comprises the TNFα inhibitor and a package insert or label providing information pertaining to use of the TNFα inhibitor for the treatment of juvenile idiopathic arthritis. In another embodiment, the information is printed on a label which is on the outside of the article of manufacture, in a position which is visible to prospective purchasers.

In one embodiment, the package insert of the invention informs a reader, including a subject, e.g., a purchaser, who will be administering the TNFα inhibitor for treatment, that the TNFα inhibitor, e.g., a TNFα antibody such as adalimumab, is an indicated treatment of juvenile idiopathic arthritis, including polyarticular JIA.

In one embodiment, the package insert of the invention describes certain therapeutic benefits of the TNFα antibody, e.g., adalimumab, including specific symptoms of juvenile idiopathic arthritis which may be reduced by using the TNFα antibody, e.g., adalimumab. It should be noted that the package insert may also contain information pertaining to other disorders which are treatable using the TNFα antibody, e.g., adalimumab. Information described herein which is provided in a package insert and pertains to other disorders, i.e., diseases other than juvenile idiopathic arthritis, is also included within the scope of the invention.

In one embodiment, the package insert of the invention describes the fixed dose amount and administration of adalimumab for the treatment of juvenile idiopathic arthritis.

In one embodiment, the article of manufacture of the invention comprises instructions regarding how to treat JIA using a fixed dose of TNF inhibitor. The package insert may indicate that Humira® (adalimumab) is indicated for reducing signs and symptoms of moderately to severely active polyarticular juvenile idiopathic arthritis in patients ages 4 years of age and older. The package insert may also indicate that Humira® (adalimumab) can be used alone or in combination with methotrexate. In one embodiment, the label indicates that adalimumab may be used to treat Juvenile Idiopathic Arthritis (JIA) by reducing signs and symptoms of moderately to severely active polyarticular juvenile idiopathic arthritis in patients ages 4 years of age and older. In another embodiment, the package insert indicates that the dosing of adalimumab for Juvenile Idiopathic Arthritis is as follows: 15 kg (33 lbs) to <30 kg (66 lbs): 20 mg every other week; and ≥30 kg (66 lbs): 40 mg every other week.

The label may indicate that therapy includes a 24 mg Ada/M² BSA dose at week 0, which is administered every other week subcutaneously. The label may also indicate that the dosing for the treatment of juvenile idiopathic arthritis with adalimumab is 24 mg Ada/M² BSA every other week. The label may also indicate that some patients with juvenile idiopathic arthritis may derive additional benefit by increasing frequency to 24 mg Ada/M² BSA every week.

In another embodiment, the package insert of the invention indicates that adalimumab is administered by subcutaneous injection for the treatment of JIA.

In one embodiment, the package insert may indicate that the recommended dose of Humira® (adalimumab) for patients 4 to 17 years of age with polyarticular juvenile idiopathic arthritis is based on weight as shown below in Table 1A. The insert may further indicate that methotrexate, glucocorticoids, salicylates, NSAIDs or analgesics may be continued during treatment with Humira® (adalimumab). In addition, the insert may indicate that limited data are available for Humira® (adalimumab) treatment in pediatric patients with a weight below 15 kg.

TABLE 1

| Pediatric Patients (4 to 17 years) | Dose |
|---|---|
| 15 kg (33 lbs) to <30 kg (66 lbs) | 20 mg every other week (20 mg Prefilled Syringe) |
| ≥30 kg (66 lbs) | 40 mg every other week (Humira ® (adalimumab) Pen or 40 mg Prefilled Syringe) |

In another embodiment, the package insert may indicate that it is recommended that juvenile idiopathic arthritis patients, if possible, be brought up to date with all immunizations in agreement with current immunization guidelines prior to initiating Humira® (adalimumab) therapy. The insert may further indicate that patients on Humira® (adalimumab) may receive concurrent vaccinations, except for live vaccines.

In another embodiment, the package insert may indicate that, in patients with juvenile idiopathic arthritis, adalimumab antibodies were identified in 16% of Humira® (adalimumab)-treated patients. The insert may further indicate that in patients receiving concomitant methotrexate, the incidence was 6% compared to 26% with Humira® (adalimumab) monotherapy.

In another embodiment, the package insert may indicate the type and frequency of adverse reactions reported in juvenile idiopathic arthritis patients during clinical studies. In various embodiments, the insert may include some or all of the following. In general, the adverse reactions in pediatric patients were similar in frequency and type to those seen in adult patients.

The label or package insert may include important findings and differences from adults are discussed in the following paragraphs.

In one embodiment, the package insert may indicate that in the juvenile idiopathic arthritis study, Humira® (adalimumab) was shown to reduce signs and symptoms of active polyarticular juvenile idiopathic arthritis in patients ages 4 to 17 years of age. The package insert may also indicate that Humira® (adalimumab) has not been studied in children less than 4 years of age, and there are limited data on Humira® (adalimumab) treatment in children with weight <15 kg. In addition, the insert may indicate that safety of Humira® (adalimumab) in pediatric patients was generally similar to that observed in adults with certain exceptions.

In another embodiment, the package insert may indicate that in subjects with juvenile idiopathic arthritis (ages 4 to 17 years of age), the mean steady-state trough serum adalimumab concentrations for subjects weighing <30 kg receiving 20 mg Humira® (adalimumab) subcutaneously every other week as monotherapy or with concomitant methotrexate were 6.8 µg/mL and 10.9 µg/mL, respectively. In another embodiment, the insert may also indicate that the mean steady-state trough serum adalimumab concentrations for subjects weighing ≥30 kg receiving 40 mg Humira® (adalimumab) subcutaneously every other week as monotherapy or with concomitant methotrexate were 6.6 µg/mL and 8.1 µg/mL, respectively.

In one embodiment, the package insert includes information regarding juvenile idiopathic arthritis clinical studies. In various embodiments, the insert may include some or all of the following.

In another embodiment, the package insert of the invention may indicate that Humira® (adalimumab) is used in adults or children (as indicated) to reduce the signs and symptoms of moderate to severe polyarticular juvenile idiopathic arthritis (JIA) in children 4 years of age and older. In yet another embodiment, the package insert may indicate that Humira® (adalimumab) can be used alone or with methotrexate or with certain other medicines.

The package insert of the invention may also provide information to subjects who will be receiving adalimumab regarding combination uses for both safety and efficacy purposes. The package insert of the invention may contain warnings and precautions regarding the use of the TNFα inhibitor, e.g., a TNFα antibody such as adalimumab. In one embodiment, the information provided in the label describes certain adverse events identified during studies of the efficacy and safety of the TNFα inhibitor.

The label of the invention may contain information regarding the use of the TNFα inhibitor, e.g., a TNFα antibody such as adalimumab, in clinical studies for juvenile idiopathic arthritis. In one embodiment, the label of the invention describes the studies described herein as the Examples, either as a whole or in portion. The label or package insert may indicate that Humira® (adalimumab) has been studied in 171 pediatric patients, aged 4 to 17 years of age, with polyarticular juvenile idiopathic arthritis (see Examples provided herein).

The label of the invention may contain information regarding adverse events. The label or package insert may indicate that severe adverse reactions reported in the study included neutropenia, streptococcal pharyngitis, increased aminotransferases, herpes zoster, myositis, metrorrhagia, appendicitis. The label or package insert may indicate that serious infections were observed in 4% of patients within approximately 2 years of initiation of treatment with Humira® (adalimumab) and included cases of herpes simplex, pneumonia, urinary tract infection, pharyngitis, and herpes zoster. The label or package insert may indicate that a total of 45% of children experienced an infection while receiving Humira® (adalimumab) with or without concomitant MTX in the first 16 weeks of treatment. The label or package insert may indicate that the types of infections reported in juvenile idiopathic arthritis patients were generally similar to those commonly seen in outpatient JIA populations. The label or package insert may indicate that upon initiation of treatment, the most common adverse reactions occurring in the pediatric population treated with Humira® (adalimumab) were injection site pain and injection site reaction (19% and 16%, respectively). The label or package insert may indicate that a less commonly reported adverse event in children receiving Humira® (adalimumab) was granuloma annulare which did not lead to discontinuation of Humira® (adalimumab) treatment. The label or package insert may indicate that in the first 48 weeks of treatment, non-serious hypersensitivity reactions were seen in approximately 6% of children and included primarily localized allergic hypersensitivity reactions and allergic rash. The label or package insert may indicate that isolated mild to moderate elevations of liver aminotransferases (ALT more common than AST) were observed in children with juvenile idiopathic arthritis exposed to Humira® (adalimumab) alone; liver function tests (LFT) elevations were more frequent among those treated with the combination of Humira® (adalimumab) and MTX. The label or package insert may indicate that, in general, these elevations did not lead to discontinuation of Humira® (adalimumab) treatment. The label or package insert may indicate that in the juvenile idiopathic arthritis trial, 10% of patients treated with Humira® (adalimumab) who had negative baseline anti-dsDNA antibodies developed positive titers after 48 weeks of treatment. The label or package insert may indicate that no patient developed clinical signs of autoimmunity during the clinical trial. The label or package insert may indicate that approximately 15% of children treated with Humira® (adalimumab) developed mild-to-moderate elevations of creatine phosphokinase (CPK). The label or package insert may indicate that elevations exceeding 5 times the upper limit of normal were observed in several patients. CPK levels decreased or returned to normal in all patients. The label or package insert may indicate that most patients were able to continue Humira® (adalimumab) without interruption.

In one embodiment of the invention, the kit comprises a TNFα inhibitor, such as an antibody, an second pharmaceutical composition comprising an additional therapeutic agent, and instructions for administration of both agents for the treatment of juvenile idiopathic arthritis. The instructions may describe how, e.g., subcutaneously, and when, e.g., at week 0, week 2, and biweekly thereafter, doses of TNFα antibody and/or the additional therapeutic agent shall be administered to a subject for treatment.

Another aspect of the invention pertains to kits containing a pharmaceutical composition comprising an anti-TNFα antibody and a pharmaceutically acceptable carrier and one or more additional pharmaceutical compositions each comprising a drug useful for treating a TNFα related disorder and a pharmaceutically acceptable carrier. Alternatively, the kit comprises a single pharmaceutical composition comprising an anti-TNFα antibody, one or more drugs useful for treating a TNFα related disorder and a pharmaceutically acceptable carrier. The kits further contain instructions for fixed dosing of the pharmaceutical compositions for the treatment of a TNFα related disorder.

The package or kit alternatively may contain the TNFα inhibitor and it may be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

Additional Therapeutic Agents

TNFα inhibitors, including antibodies, used in the methods and compositions of the invention, or antigen binding portions thereof can be used alone or in combination to treat JIA. It should be understood that the antibodies or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which effects the viscosity of the composition. In one embodiment, the TNFα antibody, or antigen-binding portion thereof, is administered with methotrexate.

It should further be understood that the combinations which are to be included within this invention are those combinations useful for their intended purpose. The agents set forth below are illustrative for purposes and not intended to be limited. The combinations, which are part of this invention, can be the TNFα inhibitors used in the present invention and at least one additional agent selected from the lists below. The combination can also include more than one additional agent, e.g., two or three additional agents if the combination is such that the formed composition can perform its intended function.

TNFα inhibitors described herein may be used in combination with additional therapeutic agents such as a Disease Modifying Anti-Rheumatic Drug (DMARD) or a Nonsteroidal Antiinflammatory Drug (NSAID) or a steroid or any combination thereof. Preferred examples of a DMARD are hydroxychloroquine, leflunomide, methotrexate, parenteral gold, oral gold and sulfasalazine. Preferred examples of non-steroidal anti-inflammatory drug(s) also referred to as NSAIDS include drugs like ibuprofen. Other preferred combinations are corticosteroids including prednisolone; the well known side effects of steroid use can be reduced or even eliminated by tapering the steroid dose required when treating patients in combination with the anti-TNFα antibodies in the methods and compositions of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD 154 (gp39 or CD40L).

Preferred combinations of therapeutic agents may interfere at different points in the autoimmune and subsequent inflammatory cascade; preferred examples include TNF antagonists such as soluble p55 or p75 TNF receptors, derivatives, thereof, (p75TNFR1gG (Enbrel™) or p55TNFR1gG (Lenercept), chimeric, humanized or human TNF antibodies, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502; U.S. Pat. No. 7,250,165; US 20030049725; PCT/US01/24785; US 20040120952; US20050123541; US20050249735; US20070298040; US20070003548; US20060018907; US20060246073; US20070196373; and US20080025976, each of which is incorporated by reference herein), and adalimumab (Humira® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451,983; and 6,448,380, each of which is incorporated by reference herein. Other combinations including TNFα converting enzyme (TACE) inhibitors; IL-1 inhibitors (Interleukin-1-converting enzyme inhibitors, IL-1RA etc.) may be effective for the same reason. In one embodiment, the methods and compositions of the invention combine a TNF inhibitor, i.e. TNF antagonist, with an IL-6 antibody, such as tocilizumab (Actemra). Other preferred combinations include Interleukin 11. Yet another preferred combination are other key players of the autoimmune response which may act parallel to, dependent on or in concert with TNF function; especially preferred are IL-18 antagonists including IL-18 antibodies or soluble IL-18 receptors, or IL-18 binding proteins. It has been shown that TNF and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The TNFα inhibitors used in the invention, including antibodies, or antigen binding portions thereof, may also be combined with agents, such as methotrexate, 6-MP, azathioprine sulphasalazine, mesalazine, olsalazine chloroquinine/ohydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGFβ), tocilizumab (Actemra), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine.

Nonlimiting additional agents which can also be used in combination with an TNFα inhibitor, e.g., TNF antibody, or antigen-binding portion thereof, to treat JIA, include, but are not limited to, the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; see e.g., *Arthritis & Rheumatism* (1994) Vol. 37, 5295; *J. Invest. Med.* (1996) Vol. 44, 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1 RA (IL-1 receptor antagonist; Synergen/Amgen); anakinra (Kineret®/Amgen); TNF-bp/s-TNF (soluble TNF binding protein; see e.g., *Arthritis & Rheumatism* (1996) Vol. 39, No. 9 (supplement), S284; *Amer. J. Physiol.—Heart and Circulatory Physiology* (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g., *Arthritis & Rheumatism* (1996) Vol. 39, No. 9 (supplement), S81); Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), 5282) and thalidomide-related drugs (e.g., Celgen); leflunomide (anti-inflammatory and cytokine inhibitor; see e.g., *Arthritis & Rheumatism* (1996) Vol. 39, No. 9 (supplement), S131; *Inflammation Research* (1996) Vol. 45, pp. 103-107); tranexamic acid (inhibitor of plasminogen activation; see e.g., *Arthritis & Rheumatism* (1996) Vol. 39, No. 9 (supplement), S284); T-614 (cytokine inhibitor; see e.g., *Arthritis & Rheumatism* (1996) Vol. 39, No. 9 (supplement), S282); prostaglandin E1 (see e.g., *Arthritis & Rheumatism* (1996) Vol. 39, No. 9 (supplement), S282); Tenidap (non-steroidal anti-inflammatory drug; see e.g., *Arthritis & Rheumatism* (1996) Vol. 39, No. 9 (supplement), S280); Naproxen (non-steroidal anti-inflammatory drug; see e.g., *Neuro Report* (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., *Arthritis & Rheumatism* (1996) Vol. 39, No. 9 (supplement), S281); Azathioprine (see e.g., *Arthritis & Rheumatism* (1996) Vol. 39, No. 9 (supplement), S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin-17 inhibitors (see e.g., *Arthritis & Rheumatism* (1996) Vol. 39, No. 9 (supplement), S120); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP 10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents.

In one embodiment, the TNFα inhibitor, e.g., TNF antibody, or antigen-binding portion thereof, is administered in combination with one of the following agents for the treatment of juvenile idiopathic arthritis: small molecule inhibitor of KDR (ABT-123), small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hcl; sulfadiazine; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; ABT-874; ABT-325 (anti-IL 18); anti-IL 15; BIRB-796; SCIO-469; VX-702; AMG-548; VX-740; Roflumilast; IC-485; CDC-801; and mesopram. In another embodiment, an TNF antibody, or antigen-binding portion thereof, is administered for the treatment of an TNF-related disorder in combination with one of the above mentioned agents for the treatment of juvenile idiopathic arthritis.

The TNFα inhibitor, e.g., antibodies, or antigen binding portions thereof, used in the methods and compositions of the invention, may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists.

The present invention is further illustrated by the following Example which should not be construed as limiting in any way. The following example describes the efficacy of adalimumab for the treatment of juvenile idiopathic arthritis (JIA), also referred to, below as juvenile rheumatois arthritis (JRA). It should be noted that the Examples provided herein represent different methods of treating JIA using a TNFα inhibitor, such as a human TNFα, antibody, or antigen-binding portion thereof. As such, data and results described in the Examples section which shows treatment of JIA using a fixed dosing regimen with a TNFα inhibitor are included in the methods of the invention. The Examples and discoveries described herein are representative of a TNFα inhibitor, e.g., adalimumab, which is effective for treating JIA on a fixed dosing regimen. As such, the studies and results described in the Examples section herein may be used as a guideline for treating JIA with a fixed dose using a TNFα inhibitor.

Example 1

Long-Term Efficacy and Safety of Adalimumab in Children with Juvenile Rheumatoid Arthritis (JRA): Converting from Body Surface Area Dosing to Fixed Dosing in the Open-Label Extension (OLE) of a Phase III Study Adalimumab (ADA), dosed at 24 mg/m2 body-surface-area (BSA) every other week (eow), has been shown to improve signs and symptoms in juvenile rheumatoid arthritis (JRA) patients in a 48-week Phase III, randomized, controlled withdrawal trial (Ruperto, N 48-*Week Data From the Study of Adalimumab in Children With Juvenile Rheumatoid Arthritis (JRA)*. Poster presented at European League Against Rheumatism 2006).

Patients in the following trial were given the option of entering an open label extension study, with initial continued BSA dosing and a subsequent switch to weight-based fixed dosing (FD).

The following study examines long term efficacy with adalimumab treatment, and compares efficacy between dosing regimens, weight-based vs. fixed dosing (FD). Thus, the objective was to evaluate differences in the efficacy and safety of ADA treatment in JRA when converting from body-surface-area (BSA) dosing to weight-based fixed dosing (FD). The primary efficacy objectives were to 1) determine continued clinical benefit at ACR Pedi 30, 50, and 70 response levels during the open-label extension period, and 2) to examine response levels after switching from BSA dosing to weight-based FD. The primary safety objective was to evaluate the long-term safety profile of adalimumab treatment.

An overview of the study is shown in FIG. 1. A total of 171 patients were enrolled in the trial. All patients received open-label adalimumab 24 mg/M2 BSA (max. dose 40 mg) given subcutaneously (sc) eow for the first 16 weeks. At the end of 16 weeks, ACR Pedi 30 responders entered the double-blind period of the trial and were randomised to either continue to receive adalimumab or to receive placebo.

Patients remained in the double-blind period of the trial for 32 weeks or until time of first flare, whichever came first. Patients who participated in the blinded period could enter into the BSA-dosed open-label extension (BSA-OLE). After at least 16 weeks of BSA-OLE participation, and upon approval of ethics committees, patients could continue into the Fixed-Dosing OLE (FD-OLE), where dosing was based on body weight (patients <30 kg received 20 mg adalimumab eow; those ≥30 kg received 40 mg adalimumab eow).

Inclusion criteria included polyarticular course JRA by ACR Criteria (any onset type), age: 4-17 years, active disease (≥5 swollen joints; ≥3 joints with limitation of motion (LOM)), prior adequate trial of NSAIDs and stable methotrexate (MTX) dosage. Exclusion criteria included Functional Class IV by ACR criteria, joint surgery within 2 months of screening, ongoing chronic or active infection, and significant active concomitant illness.

Patient retention throughout the study was good, with few discontinuations due to lack of efficacy or adverse events (patient disposition in the open-label extension is shown in Table 2). 83% of patients entering into the BSA-OLE completed this period of the study and entered into the FD portion of the study. 4 patients (3.8%) discontinued the study during the first 16 weeks of the FD-OLE. Baseline demographics and disease activity in the OLE were consistent with the open-label portion of the study, as shown in Table 3.

TABLE 2

Patient Disposition in Open-Label Extension

128 Entered BS-OLE
106 Completed
Reasons for Withdrawal:
Other (6)
Withdrew consent (9)

TABLE 2-continued

Patient Disposition in Open-Label Extension

Lack of Efficacy (4)
Adverse Event (2)
Protocol violation (1)

| 53 Entered FD-OLE at Increased Dose | 53 Entered FD-OLE at Same/Decreased dose |
|---|---|
| 50 Completed to Week 16 of FD-OLE | 53 Completed to Week 16 of FD-OLE |
| Reasons for Withdrawal: | Reasons for Withdrawal: |
| Lost to follow-up (2) | Adverse Event (1) |
| Other (1) | |

TABLE 3

Baseline Patient Characteristics and Disease Activity

| | All patients entering study (n = 171) | Patients entering BSA-OLE (n = 128) |
|---|---|---|
| Age (years) | 11 | 11 |
| JRA Duration (years) | 4.0 | 3.6 |
| Female (%) | 80 | 77 |
| Positive RF (%) | 22 | 22 |
| Physician Global | 58.2 | 58.4 |
| Parent Global | 42.9 | 48.2 |
| # Active Joints | 15.0 | 17.2 |
| # LOM Joints | 12.8 | 13.4 |
| CHAQ DI | 0.9 | 1.0 |

Values are from Day 0 of open-label phase.
Mean values, except percentages.

Patients who completed the double-blind phase or flared were eligible to continue in the open-label BSA extension period and receive open-label adalimumab, during which patients who had been on placebo rapidly recovered response. The marked ACR Pedi response rates seen in the earlier periods of the study were maintained over time, as shown in FIG. 2.

For patients entering the FD-OLE, data comparing ACR Pedi responses before and after switching to weight-based fixed dosing showed a maintenance of the ACR Pedi response, as shown in FIG. 3.

For the switch to fixed-dosing, the dosage received by patients could increase, decrease, or stay the same as that previously received during BSA-dosing. Two groups were analyzed to determine if change in dose affected response, patients who increased dose, and patients whose dosage decreased or stayed the same (these patients were grouped together because of the very small number of patients (n=3) who decreased dose). Of the 133 patients who completed the 32-week double-blind period, 128 continued to receive BSA-based dosing in the OLE. Of these, 106 patients continued to the weight-based fixed dosing period. Following the conversion, 50% (53 of 106) of patients received either the same or a lower dose of ADA (because only 3 patients received a decreased ADA dose, the dosage groups were combined for this analysis) and the other 50% received a higher dose. Previous ACR Pedi responses (Week 0) were maintained in both groups during the first 48 weeks of weight-based fixed-dosing (FIG. 4).

Previous ACR Pedi responses (Week 0) were maintained during the first 16 weeks of weight-based fixed-dosing (see Table 4).

TABLE 4

Adalimumab ACR Pedi Response Rates are Maintained in Patients who Decrease or Increase Dosage at Week 16 of the FD Period

| Response | Time on FD | Patients with same/ decreased dosage N1/N2 (% of responders) | Patients with increased dosage N1/N2 (% of responders) |
|---|---|---|---|
| PedACR30 | Wk 0 | 48/48 (100) | 49/50 (98) |
|  | Wk 16 | 46/48 (96) | 45/47 (96) |
| PedACR50 | Wk 0 | 46/48 (96) | 47/50 (94) |
|  | Wk 16 | 46/48 (96) | 45/47 (96) |
| PedACR70 | Wk 0 | 42/48 (88) | 44/50 (88) |
|  | Wk 16 | 42/48 (88) | 43/47 (92) |

Observed. N1 = responders, N2 = pts with data available.

Efficacy of ADA, as measured by American College of Rheumatology Pediatric (ACR Pedi) 30/50/70 responses achieved while patients were receiving BSA-based dosing, was also maintained for 48 weeks after the conversion to weight-based fixed dosing (Table 5).

TABLE 5

Comparison of Adalimumab ACR Pediatric Response Rates Before and After Conversion from BSA-Based Dosing to Weight-Based Fixed Dosing

| Clinical Response | Patients with same or lower dose N1/N2* (%) | Patients with higher dose N1/N2* (%) |
|---|---|---|
| ACR Pedi 30 |  |  |
| BSA-based dosing (Week 0) | 48/48 (100) | 49/50 (98) |
| Weight-based fixed dosing (Week 48) | 43/45 (96) | 44/46 (96) |
| ACR Pedi 50 |  |  |
| BSA-based dosing (Week 0) | 46/48 (96) | 47/50 (94) |
| Weight-based fixed dosing (Week 48) | 42/45 (93) | 44/46 (96) |
| ACR Pedi 70 |  |  |
| BSA-based dosing (Week 0) | 42/48 (88) | 44/50 (88) |
| Weight-based fixed dosing (Week 48) | 40/45 (89) | 42/46 (91) |

In addition, efficacy data to week 64 continued to support the flexed dose regimen based on body weight as subjects maintained PedACR responses through 64 weeks of OLE FD treatment regardless of whether they remained on the same dose/decreased dose or increased dose administered compared to the dose received during the OLE BSA period as shown in Table 6.

TABLE 6

Analysis of PedACR30/50/70/90 Responders by Stratification Level and Dose Change (Up to Week 64) Open-label Extension Fixed Dose Phase Open-label Extension Fixed Dose Population

| | MTX | | Non-MTX | |
|---|---|---|---|---|
| | Same/ Decreased Dose N = 28 | Increased Dose N = 31 | Same/ Decreased Dose N = 25 | Increased Dose N = 22 |
| Visit | N1/N2$^a$ (%) | | N1/N2$^a$ (%) | |
| PedACR30 | | | | |
| Baseline$^b$ (OLE FD) | 24/24 (100.0) | 29/29 (100.0) | 24/24 (100.0) | 20/21 (95.2) |
| Week 16 (OLE FD) | 23/24 (95.8) | 28/29 (96.6) | 23/24 (95.8) | 18/19 (94.7) |
| Week 32 (OLE FD) | 22/22 (100.0) | 24/25 (96.0) | 20/21 (95.2) | 18/18 (100.0) |
| Week 48 (OLE FD) | 20/22 (90.9) | 27/29 (93.1) | 23/23 (100.0) | 17/17 (100.0) |
| Week 64 (OLE FD) | 20/20 (100.0) | 26/27 (96.3) | 19/20 (95.0) | 16/16 (100.0) |
| PedACR50 | | | | |
| Baseline$^b$ (OLE FD) | 23/24 (95.8) | 27/29 (93.1) | 23/24 (95.8) | 20/21 (95.2) |
| Week 16 (OLE FD) | 23/24 (95.8) | 28/29 (96.6) | 23/24 (95.8) | 18/19 (94.70) |
| Week 32 (OLE FD) | 22/22 (100.0) | 23/25 (92.0) | 18/21 (85.7) | 18/18 (100.0) |
| Week 48 (OLE FD) | 20/22 (90.9) | 27/29 (93.1) | 22/23 (95.7) | 17/17 (100.0) |
| Week 64 (OLE FD) | 19/20 (95.0) | 25/27 (92.6) | 19/20 (95.0) | 16/16 (100.0) |
| PedACR70 | | | | |
| Baseline$^b$ (OLE FD) | 21/24 (87.5) | 25/29 (86.2) | 21/24 (87.5) | 19/21 (90.5) |
| Week 16 (OLE FD) | 22/24 (91.7) | 26/29 (89.7) | 21/24 (87.5) | 18/19 (94.7) |
| Week 32 (OLE FD) | 20/22 (90.9) | 21/25 (84.0) | 16/21 (76.2) | 18/18 (100.0) |
| Week 48 (OLE FD) | 19/22 (86.4) | 25/29 (86.2) | 21/23 (91.3) | 17/17 (100.0) |
| Week 64 (OLE FD) | 19/20 (95.0) | 21/27 (77.8) | 18/20 (90.0) | 15/16 (93.8) |
| PedACR90 | | | | |
| Baseline$^b$ (OLE FD) | 14/24 (58.3) | 23/29 (79.3) | 17/24 (70.8) | 14/21 (66.7) |
| Week 16 (OLE FD) | 17/24 (70.8) | 21/29 (72.4) | 19/24 (79.2) | 17/19 (89.5) |
| Week 32 (OLE FD) | 12/22 (54.5) | 18/25 (72.0) | 16/21 (76.2) | 14/18 (77.8) |
| Week 48 (OLE FD) | 14/22 (63.6) | 23/219 (79.3) | 18/23 (78.3) | 14/17 (82.4) |
| Week 64 (OLE FD) | 14/20 (70.0) | 16/27 (59.3) | 17/20 (85.0) | 1/16 (68.8) |

$^a$N1 = number of responders, N2 = the number of subjects with non-missing responses.
$^b$Response is calculated using OL lead-in phase Baseline.

Improvements from baseline values in individual response criteria were seen throughout the study, and these were maintained at Week 48 of the FD-OLE period. Improvements in tender and swollen joint counts were sustained in patients whether they maintained, decreased, or increased dosage (see FIG. 5). Physician's assessment of disease activity and pain, as well as patient-reported disability, showed continued improvements (see Table 7).

TABLE 7

Improvements in Disability and Signs/Symptoms are Maintained at Week 16 of the FD-OLE

| | % Improvement from Baseline | |
|---|---|---|
| | Same/Decreased Dose | Increased Dose |
| CHAQ | 80 | 85 |
| Active Joint Count | 94 | 95 |
| Physician Global Assessment | 86 | 90 |

CHAQ = Childhood Health Assessment Questionnaire. Data are shown only for patients who entered FD-OLE. Improvements are versus baseline values from Day 0 of open-label phase.

Adverse event rates in the FD-OLE were similar to those seen in the BSA-OLE, and no new safety signals were seen.

Discontinuations due to adverse events were low throughout the study. During the OLE-BSA period, only two patients discontinued due to adverse events (see Table 8), and during the OLE-FD period, only one patient discontinued due to an adverse event. No AEs of malignancy, congestive heart failure, demyelinating disease, opportunistic infection, Lupus-like syndrome, serious blood dyscrasias, or death were reported during the study. Adverse event rates remained stable after conversion to FD, as shown in Table 8.

TABLE 8

Adverse Event Rates remain stable after conversion to FD

| Event | BSA-OLE<br>N = 106*<br>PY = 198.1 | FD-OLE<br>N = 106<br>PY = 32.1 |
|---|---|---|
| | Events (Events/100 PYs) | |
| Infections | 290 (146) | 41 (128) |
| Serious Infections | 5 (2.5) | 1 (3.1) |
| Serious Adverse Events | 22 (11.1) | 3 (9.3) |
| Malignancies | 0 | 0 |

*Data are for patients entering the FD-OLE period.
PY = patient years.
Serious adverse events for this patient group during the BSA-OLE included abdominal pain, heamatochezia, bronchopneumonia, herpes zoster, pharyngitis, arthritis, JRA (4), speech disorder, malabsorption, appendicitis, joint dislocation, joint contracture, osteoarthritis, pregnancy, adenoidal and tonsillar hypertrophy (2). Except where noted, events occurred in one patient. The majority of events were judged not or probably not related by the investigator.
Serious adverse events during the FD-OLE included one event each of appendicitis, knee deformity, and arthritis. All events were judged not or probably not related by the investigator.

In conclusion, treatment with adalimumab provided substantial clinical improvement in children with active JRA. Marked improvements in disease severity and activity were maintained through 56 weeks of open-label treatment using body-surface-area dosing. These improvements were maintained after switching to weight-based fixed-dosing. Adalimumab was generally safe and well-tolerated in children with JRA. Adalimumab was efficacious and well-tolerated in the treatment of JRA. The high ACR Pedi 30/50/70/90 response rates achieved during BSA-based dosing were maintained during 48 weeks of weight-based fixed dosing.

Example 2

Improvements in Individual Disease Components are Sustained with Long-Term Adalimumab Therapy for Polyarticular Juvenile Idiopathic Arthritis To control symptoms and prevent increasing disability in children with active polyarticular Juvenile Idiopathic Arthritis (JIA), long-term, effective treatment that controls all aspects of the disease is necessary. Individual ACR Pedi response criteria were analyzed for the 128 patients who entered the open-label extension (OLE) of a Phase III study of adalimumab in the treatment of polyarticular JIA. Measurements of disease activity were performed at each visit, including active joint count (AJC), number of joints with limitation of passive motion (LOM), parent's or patient's assessment of patient's pain (PaP), disability index of the Children's Health Assessment Questionnaire (CHAQ DI), and physician's global assessment of disease activity (PhDA). Observed data were examined for those patients who had been treated with adalimumab throughout the study and reached more than 1 year in the OLE (Week 56; 75% of entering patients had data available). Patients entering the study had active polyarticular JIA, with clinically significant joint involvement, pain, limitation of motion, and disability in performing daily living activities. Long-term treatment with adalimumab provided marked improvements in disease activity, as shown in Table 9. The established safety profile for adalimumab remained consistent.

TABLE 9

Improvements in JIA with Adalimumab Therapy

| | AJC* | LOM** | PaP† | CHAQ DI‡ | PhDA† |
|---|---|---|---|---|---|
| Baseline | 17 | 14 | 49 | 1.05 | 57 |
| Improvement at Week 56 of OLE | 90% | 70% | 74% | 83% | 84% |

*75 joints assessed,
**69 joints assessed
†100-mm visual analog scale: greater scores = more active disease/more pain;
‡0 (best) to 3 (worst)

Example 3

Summary of Phase III Study Showing Efficacy of Fixed Dose Regimen

The safety and efficacy of Humira® (adalimumab) were assessed in a multicenter, randomized, withdrawal, double-blind, parallel-group study in 171 children (4 to 17 years old) with polyarticular juvenile idiopathic arthritis (JIA). In the study, the patients were stratified into two groups: MTX-treated or non-MTX-treated. All subjects had to show signs of active moderate or severe disease despite previous treatment with NSAIDs, analgesics, corticosteroids, or DMARDS. Subjects who received prior treatment with any biologic DMARDS were excluded from the study. The study included four phases: an open-label lead in phase (OL-LI; 16 weeks), a double-blind randomized withdrawal phase (DB; 32 weeks), an open-label extension phase (OLE-BSA; up to 136 weeks), and an open-label fixed dose phase (OLE-FD; 16 weeks). In the first three phases of the study, Humira® (adalimumab) was administered based on body surface area at a dose of 24 mg/m2 up to a maximum total body dose of 40 mg subcutaneously (SC) every other week. In the OLE-FD phase, the patients were treated with 20 mg of Humira® (adalimumab) SC every other week if their weight was less than 30 kg and with 40 mg of Humira® (adalimumab) SC every other week if their weight was 30 kg or greater. Patients remained on stable doses of NSAIDs and or prednisone (≤0.2 mg/kg/day or 10 mg/day maximum). Patients demonstrating a Pediatric ACR 30 response at the end of OL-LI phase were randomized into the double blind (DB) phase of the study and received either Humira® (adalimumab) or placebo every other week for 32 weeks or until disease flare. Disease flare was defined as a worsening of ≥30% from baseline in ≥3 of 6 Pediatric ACR core criteria, ≥2 active joints, and improvement of >30% in no more than 1 of the 6 criteria. After 32 weeks or at the time of disease flare during the DB phase, patients were treated in the open-label extension phase based on the BSA regimen (OLE-BSA), before converting to a fixed dose regimen based on body weight (OLE-FD phase).
Clinical Response:
At the end of the 16-week OL-LI phase, 94% of the patients in the MTX stratum and 74% of the patients in the non-MTX stratum were Pediatric ACR 30 responders. In the DB phase significantly fewer patients who received Humira® (adalimumab) experienced disease flare compared to placebo, both without MTX (43% vs. 71%) and with MTX (37% vs. 65%). More patients treated with Humira® (adalimumab) continued to show pediatric ACR 30/50/70 responses at Week 48 compared to patients treated with placebo. Pediatric ACR responses were maintained for up to two years in the OLE phase in patients who received Humira® (adalimumab) throughout the study.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents, and published patent applications, and patent applications cited throughout this application are incorporated herein by reference.

---

What is claimed:

1. A method for treating polyarticular juvenile idiopathic arthritis in a subject comprising subcutaneously administering adalimumab to the subject every other week, wherein 20 mg of adalimumab is administered to the subject every other week if the subject weighs at least 15 kg and less than 30 kg, or wherein 40 mg of adalimumab is administered to the subject every other week if the subject weighs more than or equal to 30 kg.

2. The method of claim 1, wherein the adalimumab is administered in combination with methotrexate.

3. The method of claim 1, wherein the subject is at least 4 years of age.

4. The method of claim 1, wherein the 20 mg of adalimumab or 40 mg of adalimumab is in a pre-filled vessel.

5. The method of claim 4, wherein the pre-filled vessel is a pre-filled syringe.

6. The method of claim 4, wherein the 20 mg of adalimumab or 40 mg of adalimumab is at a concentration of 50 mg/ml.

7. The method of claim 1, wherein the subject weighs more than or equal to 30 kg.

8. The method of claim 1, wherein the subject weighs at least 15 kg and less than 30 kg.

9. The method of claim 1, wherein the subject weights 30 kg.

10. The method of claim 2, wherein the subject is at least 4 years of age.

11. The method of claim 2, wherein the 20 mg of adalimumab or 40 mg of adalimumab is in a pre-filled vessel.

12. The method of claim 11, wherein the pre-filled vessel is a pre-filled syringe.

13. The method of claim 1, wherein the 20 mg of adalimumab or 40 mg of adalimumab is at a concentration of 50 mg/ml.

14. The method of claim 2, wherein the subject weighs more than or equal to 30 kg.

15. The method of claim 2, wherein the subject weighs at least 15 kg and less than 30 kg.

16. The method of claim 2, wherein the subject weights 30 kg.

17. A method for treating polyarticular juvenile idiopathic arthritis in a subject comprising subcutaneously administering adalimumab to the subject, wherein a mean steady state trough serum concentration of adalimumab is about 6 to 7 µg/mL or about 10 to 11 µg/mL, wherein 20 mg of adalimumab is administered to the subject if the subject weighs at least 15 kg and less than 30 kg, or wherein 40 mg of adalimumab is administered to the subject if the subject weighs more than or equal to 30 kg.

18. The method of claim 17, wherein the adalimumab is administered in combination with methotrexate.

19. The method of claim 17, wherein the subject is at least 4 years of age.

20. The method of claim 17, wherein the 20 mg of adalimumab or 40 mg of adalimumab is in a pre-filled vessel.

21. The method of claim 20, wherein the pre-filled vessel is a pre-filled syringe.

22. The method of claim 20, wherein the 20 mg of adalimumab or 40 mg of adalimumab is at a concentration of 50 mg/ml.

23. The method of claim 17, wherein the subject weighs more than or equal to 30 kg.

24. The method of claim 17, wherein the subject weighs at least 15 kg and less than 30 kg.

25. The method of claim 17, wherein the subject weights 30 kg.

26. The method of claim 17, wherein said method is a monotherapy with adalimumab, and the mean steady state trough serum concentration of adalimumab is about 6 to 7 μg/mL.

27. The method of claim 17, wherein the adalimumab is administered in combination with methotrexate, and the mean steady state trough serum concentration of adalimumab is about 10 to 11 μg/mL.

28. The method of claim 17, wherein the adalimumab is administered to the subject every other week.

29. The method of claim 28, wherein the adalimumab is administered in combination with methotrexate.

30. The method of claim 28, wherein the subject is at least 4 years of age.

31. The method of claim 28, wherein the 20 mg of adalimumab or 40 mg of adalimumab is in a pre-filled vessel.

32. The method of claim 31, wherein the pre-filled vessel is a pre-filled syringe.

33. The method of claim 31, wherein the 20 mg of adalimumab or 40 mg of adalimumab is at a concentration of 50 mg/ml.

34. The method of claim 28, wherein the subject weighs more than or equal to 30 kg.

35. The method of claim 28, wherein the subject weighs at least 15 kg and less than 30 kg.

36. The method of claim 28, wherein the subject weights 30 kg.

37. The method of claim 28, wherein said method is a monotherapy with adalimumab, and the mean steady state trough serum concentration of adalimumab is about 6 to 7 μg/mL.

38. The method of claim 28, wherein the adalimumab is administered in combination with methotrexate, and the mean steady state trough serum concentration of adalimumab is about 10 to 11 μg/mL.

* * * * *